(12) United States Patent
Janssen et al.

(10) Patent No.: US 7,785,674 B2
(45) Date of Patent: Aug. 31, 2010

(54) DELIVERY SYSTEMS FOR DELIVERING FUNCTIONAL COMPOUNDS TO SUBSTRATES AND PROCESSES OF USING THE SAME

(75) Inventors: Robert Allen Janssen, Alpharetta, GA (US); John Glen Ahles, Neenah, WI (US); Thomas David Ehlert, Neenah, WI (US); John Gavin MacDonald, Decatur, GA (US); Earl C. McCraw, Jr., Duluth, GA (US); Patrick Sean McNichols, Hortonville, WI (US); Paul Warren Rasmussen, Neenah, WI (US); Steve Roffers, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 553 days.

(21) Appl. No.: 11/777,145

(22) Filed: Jul. 12, 2007

(65) Prior Publication Data
US 2009/0017225 A1      Jan. 15, 2009

(51) Int. Cl.
*B06B 1/00*   (2006.01)
*B05D 3/00*   (2006.01)
(52) U.S. Cl. .................... 427/600; 427/565
(58) Field of Classification Search ............. 427/565, 427/600, 601; 210/748.01, 748.02
See application file for complete search history.

(56) References Cited

U.S. PATENT DOCUMENTS

| 2,307,206 A | 1/1943 | Fischer |
| 2,584,053 A | 1/1952 | Seavey et al. |
| 2,946,981 A | 7/1960 | O'Neill |
| 3,202,281 A | 8/1965 | Weston |
| 3,246,881 A | 4/1966 | Davidson et al. |
| 3,249,453 A | 5/1966 | Schnoring et al. |
| 3,273,631 A | 9/1966 | Neuman |
| 3,275,787 A | 9/1966 | Newberry |
| 3,325,348 A | 6/1967 | Bennett |
| 3,326,470 A | 6/1967 | Loudin et al. |
| 3,338,992 A | 8/1967 | Kinney |
| 3,341,394 A | 9/1967 | Kinney |
| 3,479,873 A | 11/1969 | Hermanns |

(Continued)

FOREIGN PATENT DOCUMENTS

CA        2175065        5/1995

(Continued)

OTHER PUBLICATIONS

Lei et. al. "Synthesis of Tungsten Nanoparticles by Sonoelectrochemistry" Ultrasonics Sonochemistry 14 (2007) p. 81-83; available online Apr. 4, 2006.*

(Continued)

*Primary Examiner*—Michael Cleveland
*Assistant Examiner*—Nathan H Empie
(74) *Attorney, Agent, or Firm*—Armstrong Teasdale LLP

(57) ABSTRACT

Delivery systems for incorporating functional compounds into substrates for use in various consumer products are disclosed. Specifically, the delivery system includes a carrier component comprising an ultrasonically energized and electrically charged adsorbent and one or more functional compounds. The ultrasonically energized and electrically charged adsorbent can adsorb the desired functional compounds and bind the functional compounds to the surface of the substrate.

20 Claims, 9 Drawing Sheets

U.S. PATENT DOCUMENTS

Figure 1:
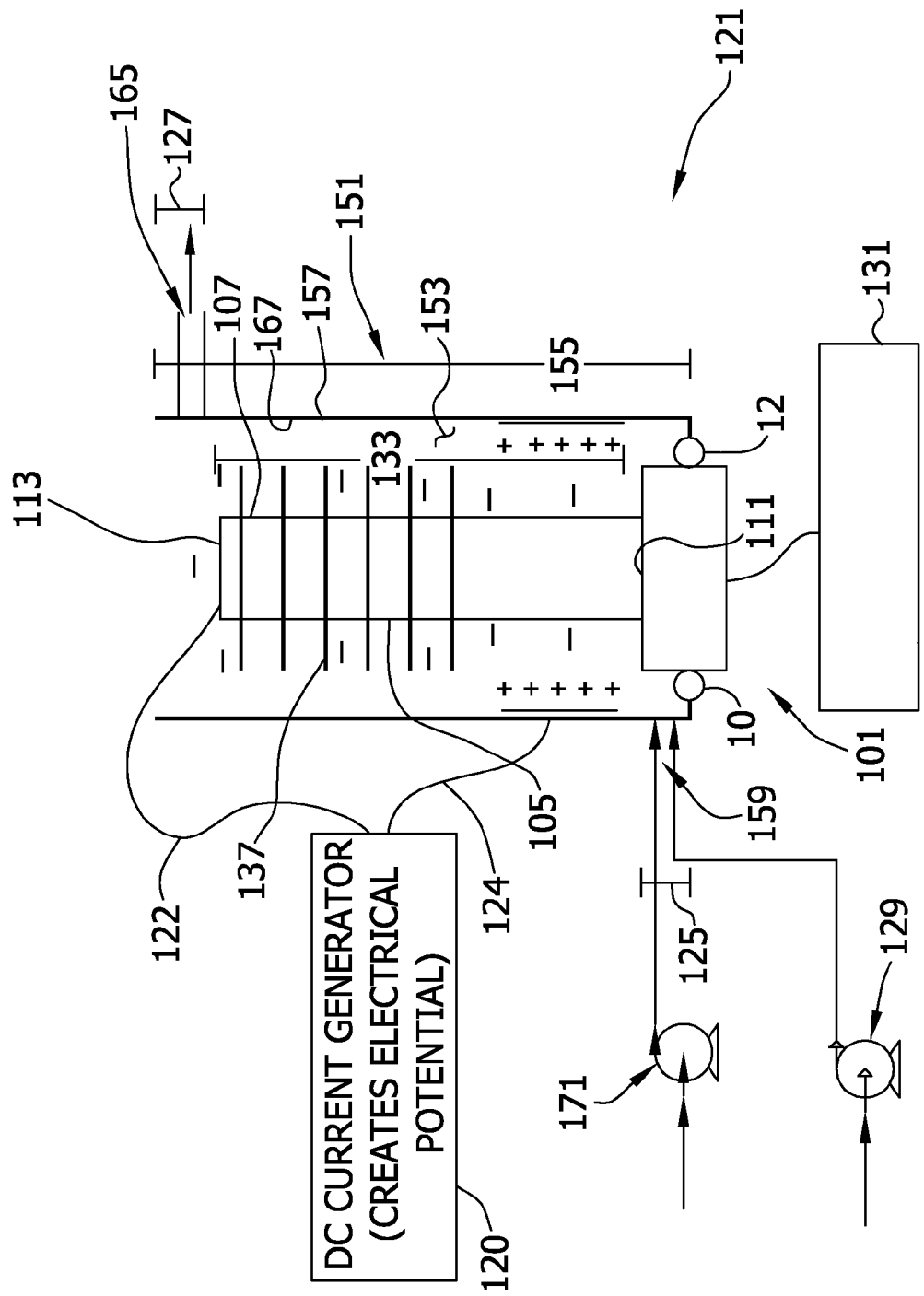

| | | |
|---|---|---|
| 3,490,584 A | 1/1970 | Balamuth |
| 3,502,763 A | 3/1970 | Hartman |
| 3,519,251 A | 7/1970 | Hammitt et al. |
| 3,542,345 A | 11/1970 | Kuris |
| 3,542,615 A | 11/1970 | Dobo et al. |
| 3,567,185 A | 3/1971 | Ross et al. |
| 3,664,191 A | 5/1972 | Hermanns |
| 3,692,618 A | 9/1972 | Dorschner et al. |
| 3,782,547 A | 1/1974 | Dieter |
| 3,802,817 A | 4/1974 | Matsuki et al. |
| 3,865,350 A | 2/1975 | Burtis |
| 4,062,768 A | 12/1977 | Elliot |
| 4,168,295 A | 9/1979 | Sawyer |
| 4,218,221 A | 8/1980 | Cottell |
| 4,259,021 A | 3/1981 | Goudy, Jr. |
| 4,266,879 A | 5/1981 | McFall |
| 4,340,563 A | 7/1982 | Appel et al. |
| 4,372,296 A | 2/1983 | Fahim |
| 4,511,254 A | 4/1985 | North et al. |
| 4,556,467 A | 12/1985 | Kuhn |
| 4,663,220 A | 5/1987 | Wisneski et al. |
| 4,673,512 A | 6/1987 | Schram |
| 4,693,879 A | 9/1987 | Yoshimura et al. |
| 4,706,509 A | 11/1987 | Riebel |
| 4,708,878 A | 11/1987 | Hagelauer et al. |
| 4,726,522 A | 2/1988 | Kokubo et al. |
| 4,743,361 A | 5/1988 | Schram |
| 4,848,159 A | 7/1989 | Kennedy et al. |
| 4,877,516 A | 10/1989 | Schram |
| 4,879,011 A | 11/1989 | Schram |
| 4,929,279 A | 5/1990 | Hays |
| RE33,524 E | 1/1991 | Schram |
| 4,983,045 A | 1/1991 | Taniguchi |
| 5,006,266 A | 4/1991 | Schram |
| 5,026,167 A | 6/1991 | Berliner, III |
| 5,032,027 A | 7/1991 | Berliner, III |
| 5,059,249 A | 10/1991 | Hays |
| 5,164,094 A | 11/1992 | Stuckart |
| 5,169,067 A | 12/1992 | Matsusaka et al. |
| 5,242,557 A | 9/1993 | Jones et al. |
| 5,258,413 A | 11/1993 | Isayev |
| 5,326,164 A | 7/1994 | Logan |
| 5,330,100 A | 7/1994 | Malinowski |
| 5,335,449 A | 8/1994 | Beatty |
| 5,391,000 A | 2/1995 | Taniguchi |
| 5,466,722 A | 11/1995 | Stoffer et al. |
| 5,536,921 A | 7/1996 | Hedrick et al. |
| 5,583,292 A | 12/1996 | Karbach et al. |
| 5,585,565 A | 12/1996 | Glascock et al. |
| 5,665,383 A | 9/1997 | Grinstaff et al. |
| 5,681,457 A | 10/1997 | Mahoney |
| 5,711,888 A | 1/1998 | Trampler et al. |
| 5,803,270 A | 9/1998 | Brodeur |
| 5,831,166 A | 11/1998 | Kozuka et al. |
| 5,840,179 A * | 11/1998 | Minkara et al. ............. 209/166 |
| 5,868,153 A | 2/1999 | Cohen et al. |
| 5,873,968 A | 2/1999 | Pike et al. |
| 5,902,489 A | 5/1999 | Yasuda et al. |
| 5,916,203 A | 6/1999 | Brandon et al. |
| 5,922,355 A | 7/1999 | Parikh et al. |
| 5,935,883 A | 8/1999 | Pike |
| 5,964,926 A | 10/1999 | Cohen |
| 5,979,664 A | 11/1999 | Brodeur |
| 6,010,592 A | 1/2000 | Jameson et al. |
| 6,020,277 A | 2/2000 | Jameson |
| 6,053,424 A | 4/2000 | Gipson et al. |
| 6,055,859 A | 5/2000 | Kozuka et al. |
| 6,060,416 A | 5/2000 | Kobata |
| 6,074,466 A | 6/2000 | Iwasa |
| 6,090,731 A | 7/2000 | Pike et al. |
| 6,169,045 B1 | 1/2001 | Pike et al. |
| 6,218,483 B1 | 4/2001 | Muthiah et al. |
| 6,221,258 B1 | 4/2001 | Feke et al. |
| 6,254,787 B1 | 7/2001 | Kimura et al. |
| 6,266,836 B1 | 7/2001 | Gallego Juarez et al. |
| 6,315,215 B1 | 11/2001 | Gipson et al. |
| 6,332,541 B1 | 12/2001 | Coakley et al. |
| 6,361,697 B1 | 3/2002 | Coury et al. |
| 6,380,264 B1 | 4/2002 | Jameson et al. |
| 6,383,301 B1 | 5/2002 | Bell et al. |
| 6,450,417 B1 | 9/2002 | Gipson et al. |
| 6,467,350 B1 | 10/2002 | Kaduchak et al. |
| 6,482,327 B1 | 11/2002 | Mori et al. |
| 6,506,584 B1 | 1/2003 | Chandler et al. |
| 6,547,935 B2 | 4/2003 | Scott |
| 6,547,951 B1 | 4/2003 | Maekawa |
| 6,551,607 B1 | 4/2003 | Minerath, III |
| 6,593,436 B2 | 7/2003 | Austin et al. |
| 6,624,100 B1 | 9/2003 | Pike et al. |
| 6,627,265 B2 | 9/2003 | Kutilek |
| 6,655,826 B1 | 12/2003 | Leanos |
| 6,659,365 B2 | 12/2003 | Gipson et al. |
| 6,676,003 B2 | 1/2004 | Ehlert et al. |
| 6,689,730 B2 | 2/2004 | Hortel et al. |
| 6,739,524 B2 | 5/2004 | Taylor-McCune et al. |
| 6,770,600 B1 | 8/2004 | Lamola |
| 6,817,541 B2 | 11/2004 | Sands et al. |
| 6,818,128 B2 | 11/2004 | Minter |
| 6,858,181 B2 | 2/2005 | Aoyagi |
| 6,878,288 B2 | 4/2005 | Scott |
| 6,883,724 B2 | 4/2005 | Adiga et al. |
| 6,890,593 B2 | 5/2005 | Tian |
| 6,897,628 B2 | 5/2005 | Gunnerman |
| 6,902,650 B2 | 6/2005 | Park et al. |
| 6,911,153 B2 | 6/2005 | Minter |
| 6,929,750 B2 | 8/2005 | Laurell et al. |
| 6,935,770 B2 | 8/2005 | Schueler |
| 6,936,151 B1 | 8/2005 | Lock |
| 7,083,764 B2 | 8/2006 | Scott |
| 7,108,137 B2 | 9/2006 | Lal et al. |
| 7,150,779 B2 | 12/2006 | Meegan, Jr. |
| 7,156,201 B2 | 1/2007 | Peshkovskiy et al. |
| 7,322,431 B2 | 1/2008 | Ratcliff |
| 7,414,009 B2 | 8/2008 | Tanaka et al. |
| 7,419,519 B2 | 9/2008 | Li et al. |
| 7,424,883 B2 | 9/2008 | McNichols et al. |
| 7,516,664 B2 | 4/2009 | Meier et al. |
| 7,582,156 B2 | 9/2009 | Tanaka et al. |
| 2001/0040935 A1 | 11/2001 | Case |
| 2002/0164274 A1 | 11/2002 | Haggett et al. |
| 2003/0048692 A1 | 3/2003 | Cohen et al. |
| 2003/0066899 A1 | 4/2003 | Gipson |
| 2003/0143110 A1 | 7/2003 | Kritzler |
| 2004/0022695 A1 | 2/2004 | Simon et al. |
| 2004/0065599 A1 | 4/2004 | Lal et al. |
| 2004/0120904 A1 | 6/2004 | Lye et al. |
| 2004/0142041 A1 | 7/2004 | MacDonald et al. |
| 2004/0187524 A1 | 9/2004 | Sen et al. |
| 2005/0000914 A1 | 1/2005 | Dahlberg et al. |
| 2005/0008560 A1 | 1/2005 | Kataoka et al. |
| 2005/0025797 A1 | 2/2005 | Wang |
| 2005/0082234 A1 | 4/2005 | Solenthaler |
| 2005/0084438 A1 | 4/2005 | Do et al. |
| 2005/0084464 A1 | 4/2005 | McGrath et al. |
| 2005/0129161 A1 | 6/2005 | Laberge |
| 2005/0207431 A1 | 9/2005 | Monai |
| 2005/0260106 A1 | 11/2005 | Marhasin |
| 2006/0000034 A1 | 1/2006 | McGrath |
| 2006/0008442 A1 | 1/2006 | MacDonald et al. |
| 2006/0120212 A1 | 6/2006 | Taniguchi et al. |
| 2007/0114306 A1 | 5/2007 | Kawakami et al. |
| 2007/0170277 A1 | 7/2007 | Ehlert |
| 2008/0061000 A1 | 3/2008 | Janssen |
| 2008/0062811 A1 | 3/2008 | Janssen |

| | | | |
|---|---|---|---|
| 2008/0063718 | A1 | 3/2008 | Janssen |
| 2008/0069887 | A1 | 3/2008 | Baran et al. |
| 2008/0155763 | A1 | 7/2008 | Janssen et al. |
| 2008/0192568 | A1 | 8/2008 | Hielscher et al. |
| 2008/0251375 | A1 | 10/2008 | Hielscher et al. |

FOREIGN PATENT DOCUMENTS

| | | | |
|---|---|---|---|
| CH | 657067 | | 8/1986 |
| CN | 1247628 | | 3/2006 |
| CN | 101153138 | | 4/2008 |
| DE | 262553 | A3 | 12/1988 |
| DE | 9017338 | | 3/1991 |
| DE | 4444525 | | 6/1996 |
| DE | 19854013 | | 5/2000 |
| DE | 19913397 | A1 | 9/2000 |
| DE | 19938254 | | 2/2001 |
| DE | 19938254 | A1 | 2/2001 |
| DE | 29825063 | | 6/2004 |
| DE | 102004040233 | | 3/2006 |
| DE | 102005025118 | | 1/2007 |
| DE | 102005034629 | | 1/2007 |
| EP | 0269941 | A1 | 6/1988 |
| EP | 0292470 | | 11/1988 |
| EP | 347891 | | 12/1989 |
| EP | 0459967 | | 12/1991 |
| EP | 0625482 | A | 11/1994 |
| EP | 0648531 | | 4/1995 |
| EP | 1954388 | | 3/2007 |
| EP | 0983968 | | 3/2008 |
| FR | 2793811 | | 11/2000 |
| GB | 1404575 | | 9/1975 |
| JP | 56028221 | | 3/1981 |
| JP | 57119853 | | 7/1982 |
| JP | 58034051 | | 2/1983 |
| JP | 62039839 | U | 3/1987 |
| JP | 6372364 | | 4/1988 |
| JP | 63104664 | | 5/1988 |
| JP | 1108081 | | 4/1989 |
| JP | 2025602 | | 1/1990 |
| JP | 02281185 | A | 11/1990 |
| JP | 03053195 | A | 3/1991 |
| JP | 3086258 | | 4/1991 |
| JP | 6228824 | | 8/1994 |
| JP | 8304388 | | 11/1996 |
| JP | 9286943 | | 11/1997 |
| JP | 10060331 | | 3/1998 |
| JP | 11133661 | | 5/1999 |
| JP | 2000158364 | | 12/1999 |
| JP | 2001017970 | | 1/2001 |
| JP | 2001252588 | | 9/2001 |
| JP | 2003103152 | A | 4/2003 |
| JP | 2004020176 | | 1/2004 |
| JP | 2004256783 | | 9/2004 |
| JP | 2005118688 | | 5/2005 |
| KR | 20020073778 | A | 9/2002 |
| KR | 1020050013858 | A | 2/2005 |
| KR | 1020050113356 | A | 12/2005 |
| WO | 9400757 | | 1/1994 |
| WO | 9420833 | | 9/1994 |
| WO | 9429873 | A | 12/1994 |
| WO | 9600318 | | 1/1996 |
| WO | 9743026 | | 11/1997 |
| WO | 9817373 | | 4/1998 |
| WO | 9844058 | | 10/1998 |
| WO | 99/33520 | | 7/1999 |
| WO | 0004978 | | 2/2000 |
| WO | 0041794 | | 7/2000 |
| WO | WO 0104382 | A1 * | 1/2001 |
| WO | 0139200 | A | 5/2001 |
| WO | 0222252 | | 3/2002 |
| WO | 0250511 | | 6/2002 |
| WO | 03012800 | | 2/2003 |
| WO | 03102737 | | 12/2003 |
| WO | 2004026452 | | 4/2004 |
| WO | 2004064487 | | 8/2004 |
| WO | 2005/011804 | | 2/2005 |
| WO | 2006037591 | | 4/2006 |
| WO | 2006043970 | A2 | 4/2006 |
| WO | 2006073645 | A1 | 7/2006 |
| WO | 2006/093804 | A | 9/2006 |
| WO | 2007060245 | A1 | 5/2007 |
| WO | 2007095871 | | 8/2007 |
| WO | 2008029379 | | 3/2008 |
| WO | 2008047259 | | 4/2008 |
| WO | 2008085806 | | 7/2008 |

OTHER PUBLICATIONS

Durant et. al. "Sonoelectroreduction of Metallic Salts: A New Method for the Production of Reactive Metallic Powders for Organometallic Reactions and Its Application in Organozinc Chemistry" Eur. J. Org. Chem. 1999, p. 2845-2851.*
U.S. Appl. No. 11/777,140, filed Jul. 12, 2007.
U.S. Appl. No. 11/777,151, filed Jul. 12, 2007.
International Search Report and Written Opinion regarding PCT/IB2008/052760, dated Feb. 17, 2009.
International Search Report and Written Opinion, PCT/IB2008/055051 (Feb. 20, 2009).
International Search Report and Written Opinion regarding PCT/IB2007/052947, dated Mar. 12, 2008.
Non-final office action regarding U.S. Appl. No. 11/617,497, dated Jun. 26, 2009.
Final Office Action Regarding U.S. Appl. No. 11/530,311, dated Jun. 23, 2009.
International Search Report and Written Opinion regarding PCT/IB2007/054892 dated May 15, 2008.
International Search Report and Written Opinion regarding PCT/IB2007/054898 dated May 15, 2008.
Non-final office action regarding U.S. Appl. No. 11/950,943, dated May 1, 2009.
J.D. Lawson, "Some Criteria for a Power Producing Thermonuclear Reactor", Proc. Phys. Soc. B70, pp. 6-10 (1957).
L.A. Artsimovich, "Controlled Thermonuclear Reactions", Gordon and Breach Science Publishers, New York, first English translation, 1964.
D.R.O. Morrison, "Cold Fusion Update No. 9", Jan. 1994, from Newsgroups sci.physics.fusion, http://www.groups.google.com.
Brenner et al, Single-bubble sonoluminescence, Reviews of Modern Physics, vol. 74, Apr. 2002, pp. 425-484.
J. Lister, Plasma Physics and Controlled Fusion 48, pp. 715-716 (2006).
U.S. Department of Energy, "Report of the Review of Low Energy Nuclear Reactions", Dec. 1, 2004 (USDOE).
U.S. Appl. No. 11/966,447, filed Dec. 28, 2007.
Peplow, Mark, "Desktop fusion is back on the table," viewed at http//nature.com/news/2006/060109/full/060109-5.html on May 4, 2007.
International Search Report and Written Opinion regarding PCT/IB2007/052988, dated Feb. 14, 2008.
Taleyarkhan, et al., "Evidence for Nuclear Emissions During Acoustic Cavitation," Science, (Mar. 8, 2002), vol. 295, pp. 1868-1873.
Kloeppel, James E. "Temperature inside collapsing bubble four times that of the sun," News Bureau, University of Illinois at Urbana-Champaign, Dated Mar. 2, 2005.
Tal-Figiel B., The Formation of Stable W/O, O/W, W/O/W Cosmetic Emulsions in an Ultrasonic Field, viewed at http://www.atypon-link.com/ICHEME/doi/abs/10.1205/cherd06199 on Oct. 19, 2007.
"Controlled Thermonuclear Fusion" viewed at http://library.thinkquest.org/17940/texts/fusion_controlled/fusion_controlled.html on Oct. 23, 2007.
Flannigan, "Measurement of Pressure and Density Inside a Single Sonoluminescing Bubble," Physical Review Letters (May 26, 2006), PRL 96.
Taleyarkhan, et al. "Additional Evidence of Nuclear Emissions During Acoustic Cavitation," Physical Review E, (Mar. 2004). vol. 69.

"Thermonuclear Fusion Energy Source for Future Generations," viewed at http://nature.com/news/2006/060109/full/060109-5.html on May 4, 2007.

Lahey, Taleyarkhan, and Nigmatulin, Bubble Power, IEEE spectrum, May 2005, pp. 39-43.

International Search Report and Written Opinion regarding PCT/IB2007/053621, dated Feb. 14, 2008.

International Search Report and Written Opinion regarding PCT/IB2007/053623, dated Feb. 14, 2008.

International Search Report and Written Opinion regarding PCT/IB2007/053622, dated Feb. 14, 2008.

U.S. Appl. No. 11/617,497, filed Dec. 28, 2006.
U.S. Appl. No. 11/617,515, filed Dec. 28, 2006.
U.S. Appl. No. 11/777,151, filed Jul. 12, 2007.
U.S. Appl. No. 11/950,943, filed Dec. 5, 2007.
U.S. Appl. No. 11/963,139, filed Dec. 21, 2007.
U.S. Appl. No. 11/963,237, filed Dec. 21, 2007.
U.S. Appl. No. 11/966,458, filed Dec. 28, 2007.
U.S. Appl. No. 11/966,472, filed Dec. 28, 2007.
U.S. Appl. No. 11/966,418, filed Dec. 28, 2007.
U.S. Appl. No. 11/965,435, filed Dec. 27, 2007.

Non-final office action regarding U.S. Appl. No. 11/617,515, dated Mar. 27, 2009.

International Search Report and Written Opinion regarding PCT/IB2007/052945, dated Feb. 1, 2008.

International Search Report and Written Opinion from PCT/IB2008/052766, dated Mar. 31, 2009.

Non-final Office Action regarding U.S. Appl. No. 12/335,231, dated Oct. 15, 2009.

European Office Action regarding European Application No. 07805228.9, dated Oct. 9, 2009.

International Search Report and Written Opinion regarding PCT/IB2008/055394, dated Sep. 28, 2009.

Blume, T. and Neis, U. "Improved wastewater disinfection by ultrasonic pre-treatment." Ultrasonics Sonochemistry, 2004, No. 11, pp. 333-336.

International Search Report and Written Opinion regarding PCT/IB2008/055395, dated Sep. 14, 2009.

International Search Report and Written Opinion regarding PCT/IB2008/055514, dated Aug. 25, 2009.

International Search Report and Written Opinion issued Aug. 18, 2009 for PCT/IB2008/055520.

International Search Report and Written Opinion issued Aug. 18, 2009 for PCT/IB2008/055517.

International Search Report and Written Opinion issued Aug. 18, 2009 for PCT/IB2008/055518.

International Search Report and Written Opinion regarding PCT/IB2008/055396, dated Jul. 29, 2009.

International Search Report and Written Opinion for PCT/IB2008/052764 mailed Apr. 2, 2009.

Non-final office action regarding U.S. Appl. No. 11/530,311, dated Nov. 5, 2008.

* cited by examiner

DELIVERY SYSTEMS FOR DELIVERING FUNCTIONAL COMPOUNDS TO SUBSTRATES AND PROCESSES OF USING THE SAME

FIELD OF DISCLOSURE

The present disclosure generally relates to delivery systems capable of delivering functional compounds to substrates for use in products. More particularly, the present disclosure relates to incorporating pharmaceutical and nutritional compounds into substrates using a delivery system with a carrier component comprising an ultrasonically energized and electrically charged adsorbent. The ultrasonically energized and electrically charged adsorbent can adsorb the desired functional compounds and bind the functional compounds to the surface of the substrate.

BACKGROUND OF DISCLOSURE

Many consumer products on today's market include functional compounds to improve the product's characteristics. The functional compounds can be any material that acts upon a substrate or otherwise provides a benefit once delivered to the desired location. Examples of functional compounds that may enhance the value of a product include pharmaceuticals that are intended to be ingested, transferred transdermally, or subcutaneously injected into a human or animal patient's body, vitamins and nutrients, and various other additives that can be similarly introduced into or onto the body of a patient.

Additionally, non-pharmaceutical functional compounds can be incorporated into consumer products to improve the product's overall value. For example, products whose use is mainly for outdoors, such as deck furniture and automobile covers, could benefit by having UV absorbing compounds (UV absorbers) incorporated onto their surfaces. By absorbing UV rays, these compounds could provide an outdoor product having improved aesthetic properties and durability.

While the desire to incorporate these types of functional compounds is known, the present methods for delivering the functional compounds to products are expensive and complex. Specifically, the present methods require the use of complex chemical formulations and long, complex chemical processes to incorporate the compounds into a delivery system to facilitate the delivery of the compounds into or onto a product.

Based on the foregoing, there is a need in the art for a process that can inexpensively and efficiently deliver functional compounds to various consumer products. Additionally, it would be advantageous if the process for delivering functional compounds was capable of allowing the functional compounds to be affixed to an adsorbent, but then capable of allowing ready release of the compounds upon the occurrence of a selected event or trigger.

SUMMARY OF THE DISCLOSURE

The present disclosure is directed to delivery systems capable of delivering functional compounds into or onto substrates for use in consumer products. Generally, the delivery systems include a carrier component comprising an ultrasonically energized and electrically charged adsorbent and a functional compound. In one embodiment, the functional compound is a pharmaceutical or nutritional compound for use in a medicament to be used in or on a human or animal patient's body. In another embodiment, the functional compound is a UV absorber for use in an outdoor product such as deck furniture.

As such, the present disclosure is directed to a process of delivering functional compounds to a substrate. The process comprising: introducing an aqueous effluent comprising at least one functional compound through at least one inlet port of an elongate housing of a treatment chamber, the housing comprising longitudinally opposite ends and an interior space, the housing being further generally closed at at least one longitudinal end, and wherein the housing comprises an adsorbent located within an interior space; ultrasonically energizing and electrically charging the adsorbent at a predetermined ultrasonic frequency and electrode potential within the housing using an electrically-charged elongate ultrasonic waveguide assembly; adsorbing the functional compound to the surface of the energized and electrically charged adsorbent to form a carrier component of a delivery system; exhausting the carrier component from at least one outlet port of the housing; and contacting the carrier component with a substrate. The electrically-charged elongate ultrasonic waveguide assembly comprises an elongate ultrasonic horn.

The present disclosure is further directed to a process of delivering functional compounds to a substrate. The process comprising: introducing an aqueous effluent comprising at least one functional compound through at least one inlet port of an elongate housing of a treatment chamber, the housing comprising longitudinally opposite ends and an interior space, the housing being further generally closed at at least one longitudinal end, and wherein the housing comprises an adsorbent located within an interior space; ultrasonically energizing and electrically charging the adsorbent at a predetermined ultrasonic frequency and electrode potential within the housing using a first electrically-charged elongate ultrasonic waveguide assembly and a second electrically-charged elongate ultrasonic waveguide assembly, wherein the first waveguide assembly and the second waveguide assembly are oriented in parallel within the housing; adsorbing the functional compound to the surface of the energized and electrically charged adsorbent to form a carrier component of a delivery system; exhausting the carrier component from at least one outlet port of the housing; and contacting the carrier component with a substrate. The first waveguide assembly comprises a first elongate ultrasonic horn and the second waveguide assembly comprises a second elongate ultrasonic horn.

The present disclosure is further directed to a process of delivering functional compounds to a substrate. The process comprising: introducing an aqueous effluent comprising at least one functional compound through at least one inlet port of an elongate housing of a treatment chamber, the housing comprising longitudinally opposite ends and an interior space, the housing being further generally closed at at least one longitudinal end, and wherein the housing comprises an adsorbent located within an interior space; ultrasonically energizing and electrically charging the adsorbent at a predetermined ultrasonic frequency and electrode potential within the housing using a first electrically-charged elongate ultrasonic waveguide assembly and a second electrically-charged elongate ultrasonic waveguide assembly, wherein both the first waveguide assembly and the second waveguide assembly independently have terminal ends, and wherein the terminal end of the first waveguide assembly faces towards the terminal end of the second waveguide assembly; adsorbing the functional compound to the surface of the energized and electrically charged adsorbent to form a carrier component of a delivery system; exhausting the carrier component from at least one outlet port of the housing; and contacting the carrier component with a substrate. The first waveguide assembly comprises a first elongate ultrasonic horn and the second waveguide assembly comprises a second elongate ultrasonic horn.

The present disclosure is further directed to a process of delivering functional compounds to a substrate. The process comprising: introducing an aqueous effluent comprising at least one functional compound through at least one inlet port of an elongate housing of a treatment chamber, the housing comprising longitudinally opposite ends and an interior space, the housing being further generally closed at at least one longitudinal end, and wherein the housing comprises an adsorbent located within an interior space; ultrasonically energizing and electrically charging the adsorbent at a predetermined ultrasonic frequency and electrode potential within the housing using a first electrically-charged elongate ultrasonic waveguide assembly and a second electrically-charged elongate ultrasonic waveguide assembly, wherein both the first waveguide assembly and the second waveguide assembly independently have terminal ends, and wherein the terminal end of the first waveguide assembly faces away from the terminal end of the second waveguide assembly; adsorbing the functional compound to the surface of the energized and electrically charged adsorbent to form a carrier component of a delivery system; exhausting the carrier component from at least one outlet port of the housing; and contacting the carrier component with a substrate. The first waveguide assembly comprises a first elongate ultrasonic horn and the second waveguide assembly comprises a second elongate ultrasonic horn.

Other features of the present disclosure will be in part apparent and in part pointed out hereinafter.

BRIEF DESCRIPTION OF THE FIGURES

FIG. 1 is a schematic of a treatment chamber for use in a process according to one embodiment of the present disclosure for delivering functional compounds to a substrate;

FIG. 2A is a schematic of a treatment chamber for use in a process according to a second embodiment of the present disclosure for delivering functional compounds to a substrate;

FIG. 2B is a top plan view of the treatment chamber of FIG. 2;

FIG. 3 a schematic of a treatment chamber for use in a process according to a third embodiment of the present disclosure for delivering functional compounds to a substrate;

FIG. 4 is a schematic of a treatment chamber for use in a process according to a fourth embodiment of the present disclosure for delivering functional compounds to a substrate;

FIG. 5 is a schematic of a treatment chamber for use in a process according to a fifth embodiment of the present disclosure for delivering functional compounds to a substrate;

FIG. 6 is a schematic of a treatment chamber for use in a process according to a sixth embodiment of the present disclosure for delivering functional compounds to a substrate; and FIG. 7 is a schematic of a treatment chamber for use in a process according to a seventh embodiment of the present disclosure for delivering functional compounds to a substrate.

FIG. 8 is a schematic of a treatment chamber according to an eighth embodiment of the present disclosure for ultrasonically treating and electrolyzing a liquid.

Corresponding reference characters indicate corresponding parts throughout the drawings.

DETAILED DESCRIPTION OF THE PREFERRED EMBODIMENT

The present disclosure is generally directed to a delivery system for delivering functional compounds to a substrate and processes for using the same. Functional compounds, as noted above, are any material that acts upon a substrate or otherwise provides a benefit once delivered to the desired location. In one embodiment, the functional compounds can be any pharmaceutical and/or nutritionally suitable substance that can provide a benefit to a location on or within a patient's body once delivered. As used herein, the term "patient" refers to both human and non-human patients. In another embodiment, the functional compounds can be used to provide a benefit to an inanimate substrate or product.

In accordance with the present disclosure, the delivery system is generally directed to the construction of a carrier component containing an energized and electrically charged adsorbent and one or more functional compounds and use of such a carrier component to selectively deliver the functional compounds contained on the component to a substrate. More particularly, the carrier component acts as a carrier for a functional compound.

Specifically, the energized and electrically charged adsorbent contained within the carrier component provides a bonding site on the surface of the component for a functional compound. The functional compounds become adsorbed onto the surface of the energized and electrically charged adsorbent. Once the functional compound is bonded to the energized adsorbent, the resulting carrier component can then be used to deliver the functional compound to a particular location. The carrier component can be used as is, for instance, or can be combined with a liquid, gel, or other vehicle which may facilitate delivery of the component depending upon the particular application. Such liquid and gel vehicles are known to those skilled in the art. The carrier component and/or vehicle can also be used in conjunction with a drug delivery apparatus, such as a bandage or modified tampon.

Various different adsorbents can be used in the present disclosure. In one particularly preferred embodiment, the adsorbent is alumina. Specifically, alumina powder alone or alumina-containing beads/particles may be used, depending upon the functional compound and the trigger for releasing it. In one embodiment, the alumina is an alumina powder, preferably a Brockmann I activated aluminum oxide powder (also referred to herein as activated alumina).

Activated alumina is manufactured by mild calcinations of aluminum hydroxide (aluminum trihydrate, boehmite), which is an intermediate in the industrial production of aluminum from Bauxite. Specifically, it is precipitated from a sodium aluminate solution. By heating the aluminum hydroxide so obtained at temperatures around 500° C., approximately 33% (by weight) constitutional water is removed, and the crystal structure of the boehmite remains intact.

Aluminas are hydrophilic and have high capacities. As such, activated alumina could suitable capture anionic dyes and surfactants, and chelate with many non-polar dyes. For example, dyes with $SO_3$—, $CO_2$—, and $PO_3$— substituents can suitably bind to the surface of activated alumina. Additionally, structures having polyhydroxy groups such as 1,2-dihydroxybenzene can suitably chelate with activated alumina. Examples of polyhydroxy containing structures can include, for example:

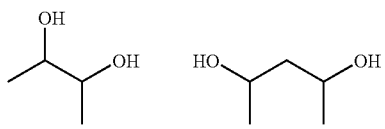

A full range of standardized aluminas are available with defined activities, pH values, and particle sizes. Activated alumina can be characterized by its Brockmann activity (e.g., activity grades of I, II, III, IV, and V), which is measured using the Brockmann and Schodder test disclosed in Brockmann & Schodder, Ber. Dtsh. Chem. Ges., 74B, 73 (1941). Generally, the activity grade is measured as follows: a standardized volume of a pair of test dyes dissolved in a standard solvent is applied to a standardized column, and after chromatographic development, the activity grade is shown by whether the test dyes separate or not. The test dye pairs that can be used are: (I) azobenzene and p-methoxyazobenzene, (II) p-methoxyazobenzene and Sudan Yellow, (III) Sudan Yellow and Sudan Red, (IV) Sudan Red and p-aminoazobenzene, and (V) p-aminoazobenzene and p-hydroxyazobenzene. Specifically, 20 milligrams of each of the two dyes from the above dye pairs is weighed into 50 milliliters of a solvent mixture containing one part pure benzene and four parts pure petroleum ether (boiling point 50-70° C.) to produce test dye solutions. Ten milliliters of each test dye solution are then applied to the top of a column containing 100-150 millimeters of the adsorbent to be tested. The columns are then eluted with 20 milliliters of eluent, which is the same mixture as used for the solvent above. To determine the activity grade, the migration distance of the test dye in front is measured. The activity grade is then given by the number of the pair of test dyes, in addition to the distance, in millimeters, from the top of the column to the front of the foremost migrated dye. An activated alumina having a Brockmann I Activity is the most reactive.

Brockmann I activated alumina can be converted to grades of lower activity by simply adding water. Specifically, to convert a Brockmann I activated alumina to a Brockmann II activated alumina, 3% (by total weight activated alumina powder) water is added to the Brockmann I activated alumina. To convert the grade I activated alumina to a grade III activated alumina, 6% (by total weight activated alumina powder) water is added, for grade IV, 10% (by total weight activated alumina powder) water is added to the Brockmann I activated alumina, and for grade V, 15% (by total weight activated alumina powder) water is added.

Examples of suitable Brockmann I activated alumina powders are commercially available from CAMAG Scientific Inc. (Wilmington, N.C.) and Sigma-Aldrich (St. Louis, Mo.).

In another embodiment, the alumina can be a particle such as an alumina or silica bead or particle. The types of particles to be used depend on the functional compound and the trigger for releasing it. For example, in one particular embodiment, the alumina particles are activated alumina particles produced from the activated alumina powder described above.

Another suitable alumina particle is an alumina particle that can contain various other ingredients. In general, the particle can contain any material that does not adversely interfere with the ability of the functional compound to bond to alumina. In this regard, at least a portion of the alumina contained by the particle should be present on the surface of the particle so that the alumina is available for adsorbing the functional compound.

For example, in one embodiment, the alumina particles for use in delivering the functional compounds are alumina sol particles. Alumina sols are colloidal hydrous alumina that can maintain a wide range of viscosities and are highly heat resistant. Many different types of alumina sols are commercially available with varying particle sizes. Of particular advantage, alumina sols can be prepared that carry a relatively strong positive surface charge or zeta potential. In this embodiment, the particle that is reacted with the functional compound contains primarily, and in some embodiments, exclusively alumina. Examples of alumina particle materials include Aluminasol-100 and Aluminasol-200, which are both commercially available from Nissan Chemical America (Houston, Tex.).

In another embodiment, the particle can contain a core material coated with alumina. The alumina can form a continuous or a discontinuous coating over the particle. The core material can be, for instance, an inorganic oxide, such as silica. For example, in one embodiment, silica sols can be used that contain silica nanoparticles that have an alumina surface coating. Such sols are commercially available from Nissan Chemical America (Houston, Tex.). The silica is coated with alumina to provide stability to the sols over certain pH ranges. In fact, alumina coated silica sols may have greater stability in some applications of the present disclosure in comparison to pure alumina sols. Specific examples of alumina coated particles with silica cores include SNOWTEX-AK®, available from Nissan Chemical America (Houston, Tex.) and Ludox Cl®, available from Grace Davison (Columbia, Md.).

When the alumina is in particle form, the particles have an average particle size of from about 5 nanometers to less than 500 microns. More suitably, the alumina particles have an average particle size of from about 10 nanometers to less than 1 micron, and even more suitably, from about 15 nanometers to about 25 nanometers.

Other adsorbent materials are also suitable for use in the present disclosure. Examples include activated carbon and zeolites. Activated carbon is hydrophobic in nature and generally favors organic materials.

Generally, zeolites are hydrated alumino-silicate minerals with porous structures. They are hydrophilic with polar, regular channels, and are typically used in air separation and dehydration.

It has now been discovered that using an energized and electrically charged adsorbent provides for improved adsorption of the functional compounds onto the surface of the adsorbent. Generally, it has been found that an adsorbent that has been energized using ultrasonic energy and electrically charged using an electric current source, such as described more fully below, can more efficiently and more effectively bind to functional compounds, allowing for an improved delivery of these functional compounds to substrates. Specifically, by subjecting the adsorbent in the ultrasonic treatment system to ultrasonic energy, microcavitation within the fluid containing the functional compounds will occur. As the small bubbles produced through microcavitation collapse or oscillate, microconvective currents are produced, which result in a flow of fluid in an otherwise stagnant zone. Additionally, the acoustic wave produced by the ultrasonic energy produces a pulsed bulk motion that further provides for fluid agitation. The increased fluid flow produced by both the microcavitation and the acoustic wave results in reducing the thickness of the hydrodynamic boundary layer that surrounds the adsorbent. This effect allows for improved mass transport of the functional compounds in the fluid to the surface of the adsorbent, allowing for a quicker, more effective adsorption.

Furthermore, by electrically charging the adsorbent, electrostatic forces can cause greater binding between the adsorbent and the functional compound. Specifically, as described more fully below, the adsorbent can become negatively or positively charged depending upon the direction and strength of the electrode potential. As such, when a more negatively charged functional compound is desired to be applied to a substrate, an electrode potential can be produced within the treatment chamber to more positively charge the adsorbent (e.g., adsorbent as an anode), which will cause a stronger attraction and binding between the more positive adsorbent and the negative functional compound. Specifically, the positively charged adsorbent is attracted to the cathode (i.e., negatively charged). This attraction further enhances the positive charge of the adsorbent, thereby enhancing the effectiveness of adsorption of negatively charged functional compounds. Likewise, when the desired functional compound carries a more positive charge, a negatively charged adsorbent can be electrically charged to enhance its negative charge as described above; that is, the adsorbent shows the properties of a cathode (e.g., negatively charged) within the treatment chamber.

In addition to the energized adsorbent, the carrier component of the delivery system of the present disclosure includes one or more functional compounds. The functional compounds for use in the processes of the present disclosure can include any suitable pharmaceutical, nutritional, or other functional compound containing at least one of the following moieties: $SO_3-$, $CO_2-$, $PO_3-$,

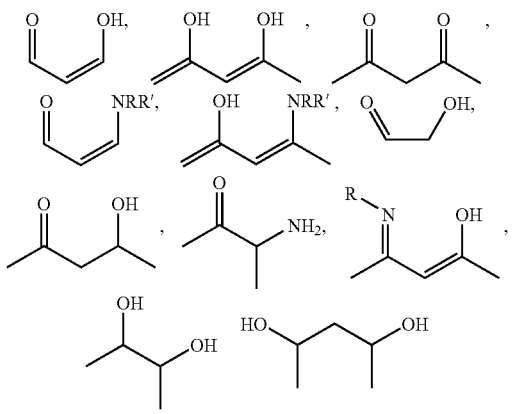

a tautomer thereof, or a functional equivalent thereof, wherein R and R' independently comprise a hydrogen, an alkyl group, or an aryl group. As used herein, a "functional equivalent" to one of the above moieties refers to functional compounds that include similar reactive groups as shown above, but which are not positioned on the molecule exactly as shown above and yet will bond with the energized adsorbent in a similar manner. Furthermore, it should be understood that various additional R groups may be included with the above moieties as long as the R groups do not interfere with the bond that is formed with the energized adsorbent.

The above moieties may form a relatively strong bond to the energized adsorbent surface. Without wishing to be bound by theory, it is believed that the above moieties form a bidentate ligand bonding system with the adsorbent's surfaces. Specifically, it is believed that the adsorbent forms a covalent bond and a coordinate bond with the above moieties. Furthermore, it is believed that a surface reaction occurs causing the functional compound to remain on the surface of the energized adsorbent (unless triggerably released) and form a coating thereon. The functional compound can cover the entire resulting adsorbent-containing carrier component or can be located at particular locations on the carrier component. Further, it should be understood that the components of the present disclosure can contain more than one functional compound so as to deliver multiple treatments to a substrate.

Generally, the functional compounds include pharmaceuticals, xenobiotics, therapeutic agents, nutritional agents, anti-viral agents, anti-microbial agents, UV absorbers, and signal agents. "Xenobiotics" is a general term used to describe any chemical interacting with an organism that does not occur in the normal metabolic pathways of that organism.

One suitable example of a therapeutic compound that may be used in the present delivery system is hydrocortisone. Hydrocortisone is a natural anti-inflammatory hormone of the glucocorticoid family of hormones produced by the adrenal cortex. Hydrocortisone has the structural formula:

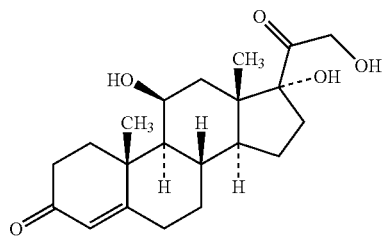

Another suitable pharmaceutical that can be used as the therapeutic compound of the delivery system is an anti-microbial. One particularly preferred anti-microbial is tetracycline, which is an antibiotic substance produced by *Streptomyces spp*. Tetracycline has the structural formula:

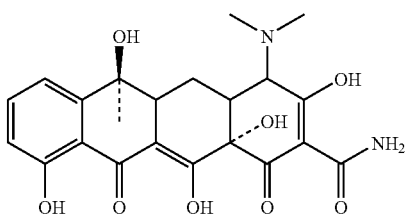

Another preferred anti-microbial is an antifungal. Examples of antifungal compounds include salicylanilide and albofungin, which have the structural formulas:

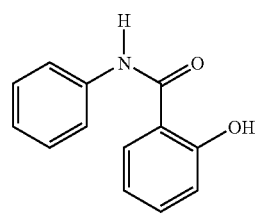

Salicylanilide

-continued

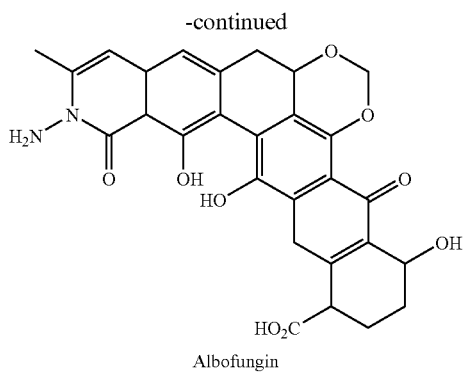

Albofungin

In yet another embodiment, antiviral compounds can be used as the functional compounds in the delivery system of the present disclosure. For example, in one particular embodiment, the antiviral compound is an anthraquinone dye. Anthraquinone dyes include, for example, Acid Green 25 (also referred to as Alizarine Cyanine Green F), Alizarin Red S, Quinalizarin, and Hypericin. The structural formulas for these anthraquinone dyes are shown below:

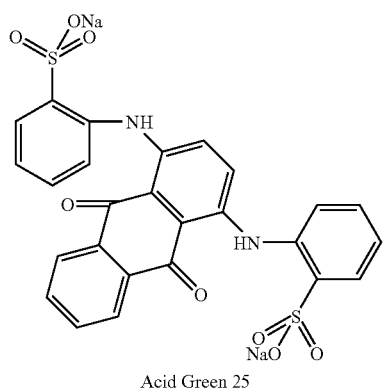

Acid Green 25

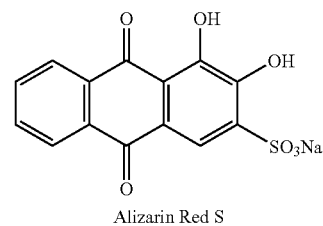

Alizarin Red S

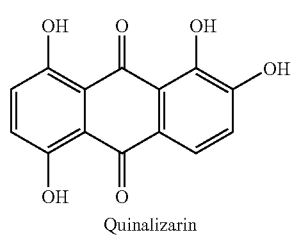

Quinalizarin

-continued

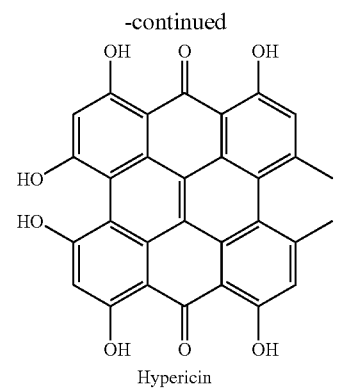

Hypericin

Other suitable pharmaceuticals can include Baicalin Hydrate, Baicalein, and Daunorubicin, which have been used as anticancer drugs by blocking proliferation and increasing apoptosis in human umbilical vascular endothelial cells. The formulas for these pharmaceuticals are shown below:

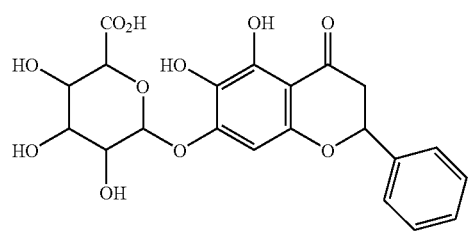

Baicalin Hydrate

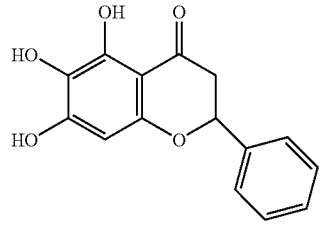

Baicalein

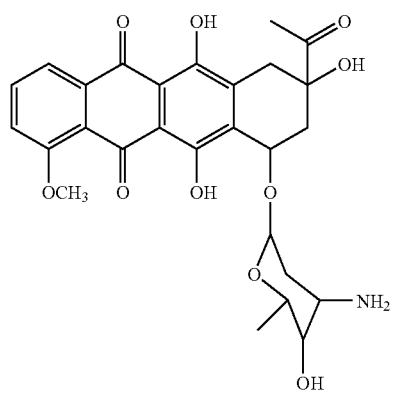

Daunorubicin

Still additional pharmaceutical compounds which may be used in the delivery system of the present disclosure include salicylamide, salacetamide, and salsalate, which are analgesic, antipyretic, and anti-inflammatory compounds. The structural formulas for these compounds are provided below:

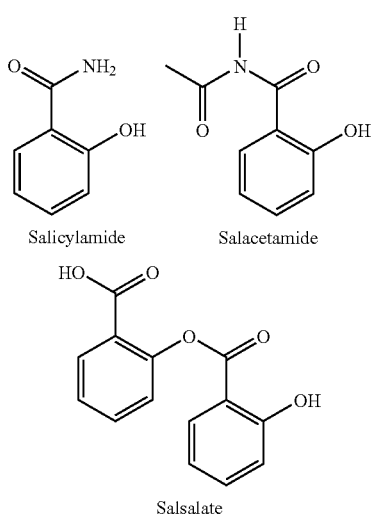

Salicylamide    Salacetamide

Salsalate

In addition to pharmaceutical compounds, nutritional compounds can be used as the functional compounds in the delivery system. Examples of nutritional compounds for use in the delivery system can include ascorbic acid (Vitamin C) and aspartame (phenylalanine). Ascorbic acid and aspartame have the structural formulas:

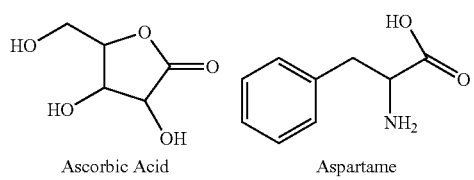

Ascorbic Acid    Aspartame

In another embodiment, the delivery system delivers ultraviolet (UV) absorbers to a substrate. UV absorbers are commonly used in products to slow down the product breakdown caused by exposure to sunlight. For example, UV absorbers can be used in products such as automobile covers, boat covers, deck furniture, and the like. UV absorbers are also useful in sunscreens and sunblocks. For example, suitable UV absorbers can include hydroxybenzophenones, which act as UV blockers by adsorbing the radiation and emitting the energy by an alternative pathway. Particularly preferred hydroxybenzophenones are 2,2'-dihydroxybenzophenone and 2,2',4,4'-tetrahydroxybenzophenone, whose chemical structures are shown below:

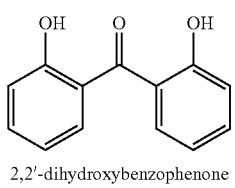

2,2'-dihydroxybenzophenone

-continued

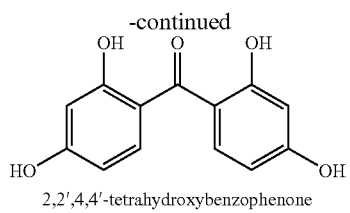

2,2',4,4'-tetrahydroxybenzophenone

Other suitable UV absorbers include radical inhibitors. These compounds terminate polymer free radicals and stop the further breakdown of the polymer chains.

Of particular advantage, in many embodiments, it has also been discovered that a functional compound can be bonded to the energized and electrically charged adsorbent without significantly impacting the positive surface charge of the energized adsorbent, which can be measured as zeta potential. The term "zeta potential" as used herein means a potential gradient that arises across an interface. This term particularly refers to the potential gradient that arises across the interface between the Stern layer in contact with the carrier component of the delivery system of the present disclosure and the diffuse layer surrounding the component. Zeta potential measurements can be taken using, for example, a Zetapals instrument which is commercially available from the Brookhaven Instrument Corporation (Holtsville, N.Y.). In general, zeta potential measurements can be conducted by adding one to three drops of a sample into a cuvet containing 1 mM KCl solution, and using the instrument's default functions preset for aqueous solutions.

Thus, once the energized and electrically charged adsorbent is bonded to the functional material, the resulting carrier component continues to maintain a relatively strong positive charge. For example, carrier components made according to the processes set forth below can have a zeta potential of greater than 20 mV, suitably greater than 30 mV, and even more suitably, greater than 40 mV. By remaining positively charged, the components are well suited for being affixed to substrates that carry a negative surface charge through coulombic attraction. Furthermore, as noted above, by electrically charging the adsorbent using an electric current source, the charge on the adsorbent can become more positive or less positive depending upon the desired functional component. Depending upon the type of carrier component produced and the surface of the substrate, the bond of the carrier component in some embodiments can be relatively permanent and substantive. Consequently, the delivery system of the present disclosure can be used to affix functional compounds to various substrates without the use of chemical binders or other attachment structures. As an example, the carrier component of the delivery system can include along its surface a pharmaceutical functional compound, and yet the carrier component may still retain sufficient positive charge to allow it to be attached to a negatively charged bandage or other topically contacting substrate. Then upon the occurrence of a specific chemical or environmental stimulus, the functional compound contained on the carrier component can be selectively released to the body of a patient, and the carrier components will remain affixed to the bandage.

In a further embodiment, a signal agent, such as a fragrance or perfume, may be used by itself or in conjunction with one of the other functional compounds described above in the carrier component of the delivery system to both treat a substrate, and also to provide an indication to the consumer of the effectiveness of such treatment or the occurrence of a particular event. By way of example, a fragrance may be adsorbed to one bonding site of the energized adsorbent and an antibiotic may be adsorbed to a second bonding site of the energized adsorbent to form the carrier component of the delivery system. The delivery system can then be delivered to an infected site. Upon removal of the infection, and the return to a more normal acidic environment, the fragrance may be released, thereby providing an indication of the effective treatment of the infection.

One particularly preferred fragrance is the alkaline fragrance, salicyladehyde, which has the formula:

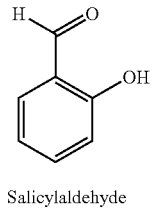

Salicylaldehyde

Other suitable signal agents can include dyes such as carminic acid and the like.

In a further example, the signal can be used to generate an indication of a particular event, such as the release of body fluids or exudates as in a bandage or a personal care product, such as a feminine care product or child care diaper product. For example, carminic acid on energized alumina would be released and change color when exposed to cadaverine, putrescine, or ammonia, which are indications of wound infection.

The carrier components used in the delivery system of the present disclosure can be present in various forms, shapes, and sizes depending upon the desired result. For example, the carrier components can be a sphere, a crystal, a rod, a disk, a tube, or a string of particles. The size of the carrier component can also vary dramatically. For instance, in one embodiment, the carrier component can have an average dimension of less than 1 millimeter. More suitably, the carrier component can have an average dimension of less than 500 microns, and even more suitably, of less than 100 microns. As used herein, the average dimension of the carrier component refers to the average length, width, height, or diameter of the carrier component.

As noted above, the general process for using the delivery system to deliver functional compounds to a substrate comprises: (1) introducing an aqueous effluent comprising at least one functional compound through at least one inlet port of an elongate housing of a treatment chamber; (2) ultrasonically energizing and electrically charging an adsorbent at a predetermined ultrasonic frequency and electrode potential within the housing using an electrically charged elongate ultrasonic waveguide assembly comprising an elongate ultrasonic horn; (3) adsorbing the functional compound to the surface of the energized and electrically charged adsorbent to form a carrier component for a delivery system; (4) exhausting the carrier component from at least one outlet port of the housing; and (5) contacting the carrier component in the delivery system with a substrate.

To begin the process, an adsorbent is energized using ultrasonic energy and, further, electrically charged using an electrode potential. Specifically, in one suitable embodiment, an alumina powder or alumina-containing particle as described above is contacted with ultrasonic energy produced by the ultrasonic waveguide assembly as described below.

The energized adsorbent is then contacted with one or more functional compounds to adsorb the functional compound to the surface of the energized adsorbent. In one embodiment, the adsorption of the functional compound to the adsorbent takes place in a batch process. When adsorbing using a batch process, one or more functional compounds are dissolved in an aqueous solution with stirring at a rate of from about 5 revolutions per minute (rpm) to about 800 rpm in a storage tank. Suitably, the aqueous solution contains from about 0.1% (by weight) to about 50% (by weight) functional compounds with the balance being water. The aqueous solution typically has a temperature of from about 20° C. to about 90° C. and a pH of from about 2.0 to about 10. An ultrasonic horn, such as described above, is placed into this tank to activate the adsorbent. Furthermore, an electrical current source, such as a DC current generator, can be connected both to the sidewall of the storage tank and to the horn using electrical wires to create an electrode potential within the tank. Adsorbent is then slowly added and activated with ultrasonic energy produced by the ultrasonic horn operating at a frequency of from about 15 kHz to about 100 kHz, more suitably at a frequency of from about 15 kHz to about 60 kHz, and even more suitably, from about 20 kHz to about 40 kHz. The adsorbent is electrically charged with an electrode potential, produced by the generator, being in the range of from about 0.1V to about 15V and, more suitably, from about 0.5V to about 5.0V and, even more suitably, from about 1.0V to about 3.0V. The mixture is stirred for about 10 seconds to about 10 minutes, suitably from about 5 minutes to about 10 minutes, to allow the functional compounds to bind to the surface of the energized and electrically charged adsorbent.

In another embodiment, the energizing of the adsorbent and the adsorption of the functional compound to the adsorbent takes place in a continuous treatment system. Typically, the treatment chamber of the continuous treatment system contains from about 10% (by void volume) to about 90% (by void volume) adsorbent. More suitably, the adsorbent present in the chamber in an amount of from about 30% (by void volume) to about 70% (by void volume).

FIG. 1 provides a treatment chamber, generally indicated at 121, to be used in the processes of the present disclosure to energize and electrically charge adsorbents in accordance with one embodiment of the present disclosure. As illustrated in FIG. 1, the treatment chamber 121 is generally elongate and has a general inlet end 125 (a lower end in the orientation of the illustrated embodiment) and a general outlet end 127 (an upper end in the orientation of the illustrated embodiment). The treatment chamber 121 is configured such that fluid (e.g., aqueous effluent containing functional compounds to be adsorbed to an adsorbent and added to a substrate) enters the treatment chamber 121 generally at the inlet end 125 thereof, flows generally longitudinally within the chamber (e.g., upward in the orientation of illustrated embodiment) and exits the chamber generally at the outlet end 127 of the chamber.

The terms "upper" and "lower" are used herein in accordance with the vertical orientation of the treatment chamber 121 illustrated in the various drawings and are not intended to describe a necessary orientation of the chamber in use. That is, while the chamber 121 is most suitably oriented vertically, with the outlet end 127 of the chamber above the inlet end 125 as illustrated in the various drawings, it is understood that the chamber may be oriented with the inlet end above the outlet end, or it may be oriented other than in a vertical orientation (see FIGS. 4-6) and remain within the scope of this disclosure.

The terms "axial" and "longitudinal" refer directionally herein to the vertical direction of the chamber 121 (e.g., end-to-end such as the vertical direction in the illustrated embodiment of FIG. 1). The terms "transverse", "lateral" and "radial" refer herein to a direction normal to the axial (e.g., longitudinal) direction. The terms "inner" and "outer" are also used in reference to a direction transverse to the axial direction of the treatment chamber 121, with the term "inner" referring to a direction toward the interior of the chamber and the term "outer" referring to a direction toward the exterior of the chamber.

The inlet end 125 of the treatment chamber 121 is in fluid communication with a suitable intake system, generally indicated at 129, that is operable to direct one or more aqueous effluents to, and more suitably through, the chamber 121. Although not illustrated, it should be understood by one skilled in the art that the intake system 129 may comprise one or more pumps operable to pump the respective effluents from a corresponding source thereof to the inlet end 125 of the chamber 121 via suitable conduits (not shown).

It is understood that the intake system 129 may be configured to deliver more than one aqueous solution to the treatment chamber 121 without departing from the scope of this disclosure. It is also contemplated that intake systems other than that illustrated in FIG. 1 and described herein may be used to deliver one or more effluents to the inlet end 125 of the treatment chamber 121 without departing from the scope of this disclosure.

Furthermore, the inlet end 125 may be in fluid communication with an air sparge, generally indicated at 171, designed to force air into the interior of the housing. The air sparge 171 facilitates the flow of liquid (e.g., aqueous effluent) transversely inward toward the horn to thereby facilitate ultrasonic energization (i.e., agitation) of the liquid. Typically, the air is forced through a porous media so as to create small air bubbles. Desirably, the air sparged used in the treatment chamber has a gas diffuser porosity rated from medium to fine and a gas flow rate of from about 0.01 liters per minute to about 100 liters per minute and, more suitably, from about 10 liters per minute to about 50 liters per minute. Furthermore, the air sparge forces air into the interior of the housing at a gas pressure of from about 0.2 psi to about 100 psi and, more suitably, from about 10 psi to about 50 psi, depending upon the desired gas flow rate and back pressure of the treatment system.

Figure 2A:
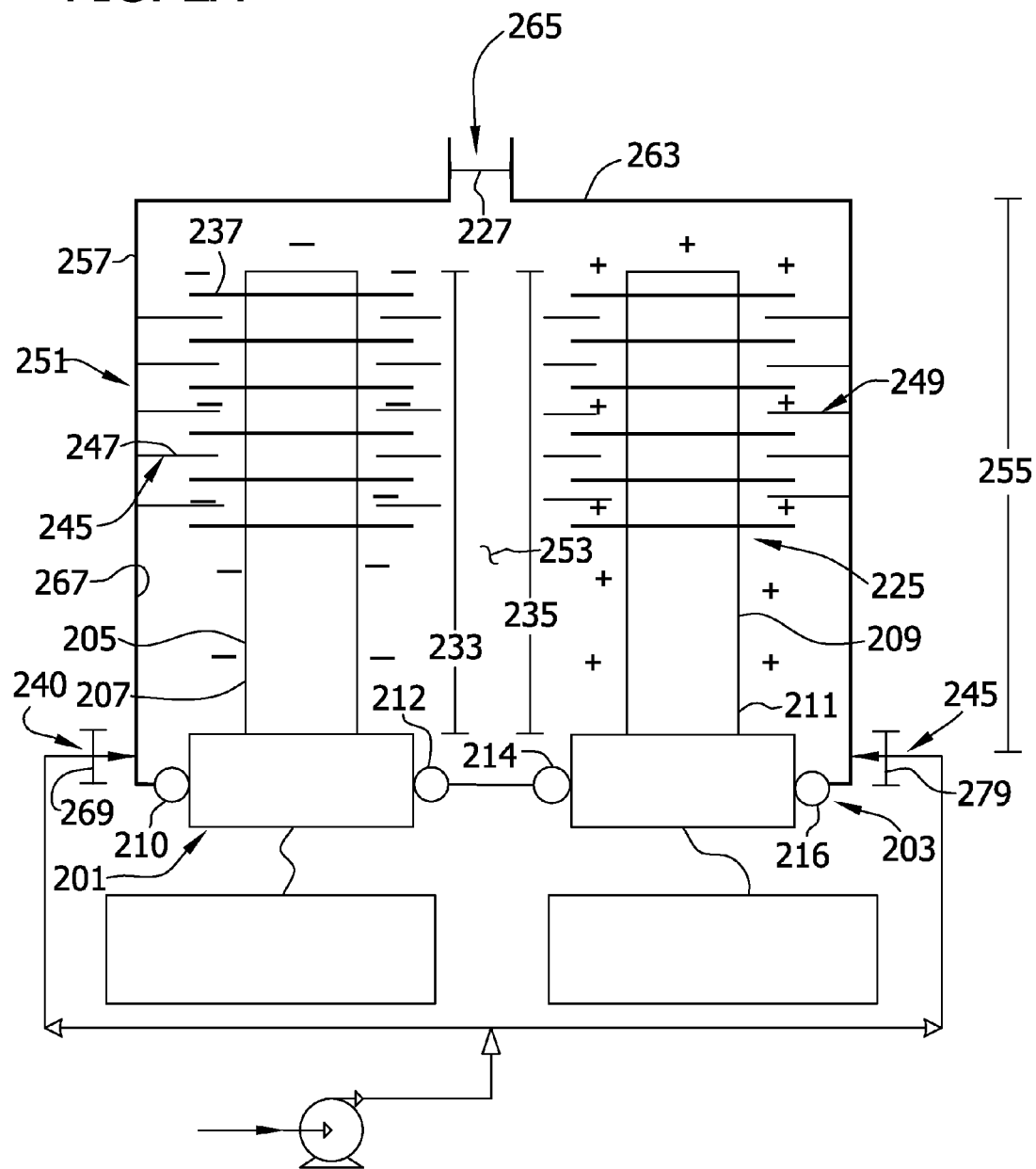

Still referring to FIG. 1, the treatment chamber 121 comprises a housing 151 defining an interior space 153 of the chamber through which liquid delivered to the chamber flows from the inlet end 125 to the outlet end 127 thereof. The housing 151 suitably comprises an elongate tube 155 generally defining, at least in part, a sidewall 157 of the chamber 121. The tube 155 may have one or more inlet ports (one such inlet port being illustrated in FIG. 1 and indicated at 159) formed therein through which one or more effluents to be treated within the chamber 121 are delivered to the interior space 153 thereof. It should be understood by one skilled in the art that the inlet end of the housing may include more than one port. For example, although not shown, the housing may comprise two inlet ports, wherein the first inlet port and the second inlet port are suitably in parallel, spaced relationship with each other. Furthermore, as illustrated in FIG. 2A, the housing may comprise two inlet ends 269 and 279. The two inlet ends 269 and 279 may further independently include at least one inlet port (indicated generally at 235 and 245, respectively).

Moreover, in one suitable embodiment, the housing further comprises an inlet collar (not shown) that is connected to and mounted on one end of the tube to further define (along with the inlet port) the inlet end of the chamber. The inlet collar at the inlet end of the chamber is generally annular and has at least one, and more suitably a plurality of inlet ports formed therein for receiving aqueous effluents into the interior space of the chamber. At least one inlet port is oriented generally tangentially relative to the annular collar so that liquid flows into the interior space of the chamber generally tangentially thereto to impart a swirling action to liquid as it enters the chamber. More suitably, a pair of inlet ports is arranged in parallel alignment with each and extends generally tangentially relative to the annular collar, with one port being designated herein as the outer inlet port and the other port being designated the inner inlet port.

This dual tangential inlet port arrangement is particularly useful for initiating mixing of components within the effluent before the effluent is further subjected to ultrasonic treatment and electric charge within the chamber. This action, combined with the swirling action resulting from the tangential direction in which the aqueous effluent are directed into the chamber, facilitate an initial mixing of these components before the aqueous effluent flows further through the chamber for ultrasonic and electric treatment. If additional components are to be added to the mixture, such components may be delivered into the interior space of the chamber via the inlet port formed in the chamber sidewall. The collar may also have an additional tangential set of inlet ports and a pair of generally vertically oriented inlet ports. It is understood, however, that none of the ports need to be oriented tangentially relative to the collar to remain within the scope of this disclosure. It is also contemplated that the collar may be omitted altogether such that all components are delivered to the inlet port formed in the chamber sidewall.

With reference to FIG. 2A, in one embodiment, the housing 251 may comprise a closure 263 connected to and substantially closing the longitudinally opposite end of the sidewall 257, and having at least one outlet port 265 therein to generally define the outlet end 227 of the treatment chamber 221. The sidewall 257 (e.g., defined by the elongate tube 255) of the chamber 221 has an inner surface 267 that together with the waveguide assembly (or waveguide assemblies described further below, and generally indicated at 201 and 203) and the closure 263 define the interior space 253 of the chamber. In the illustrated embodiment, the tube 255 is generally cylindrical so that the chamber sidewall 257 is generally annular in cross-section. However, it is contemplated that the cross-section of the chamber sidewall 257 may be other than annular, such as polygonal or another suitable shape, and remains within the scope of this disclosure. The chamber sidewall 257 of the illustrated chamber 221 is suitably constructed of a transparent material, although it is understood that any suitable material may be used as long as the material is compatible with the liquid solutions being treated in the chamber, the pressure at which the chamber is intended to operate, and other environmental conditions within the chamber such as temperature.

Figure 4:
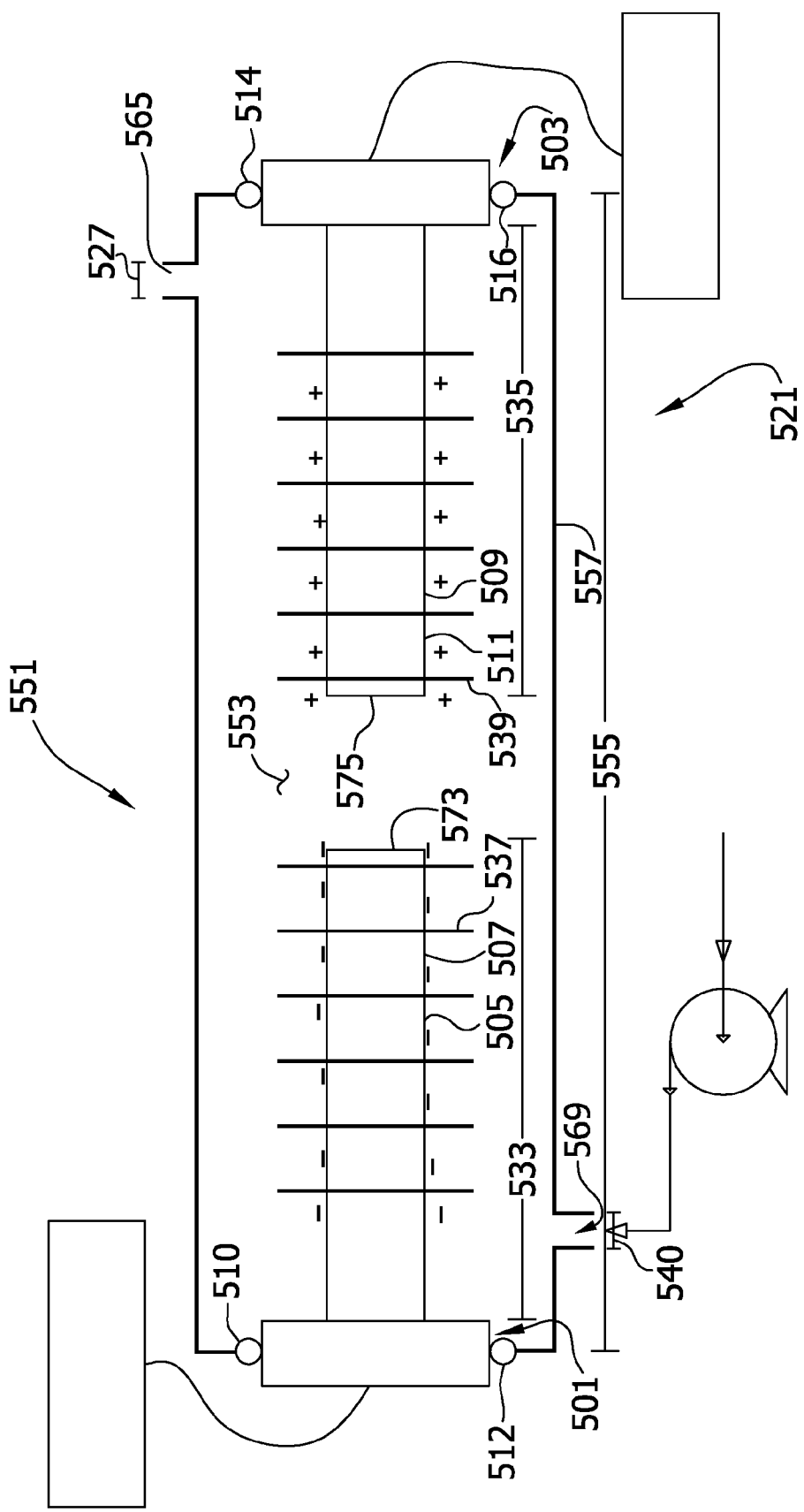
Figure 5:
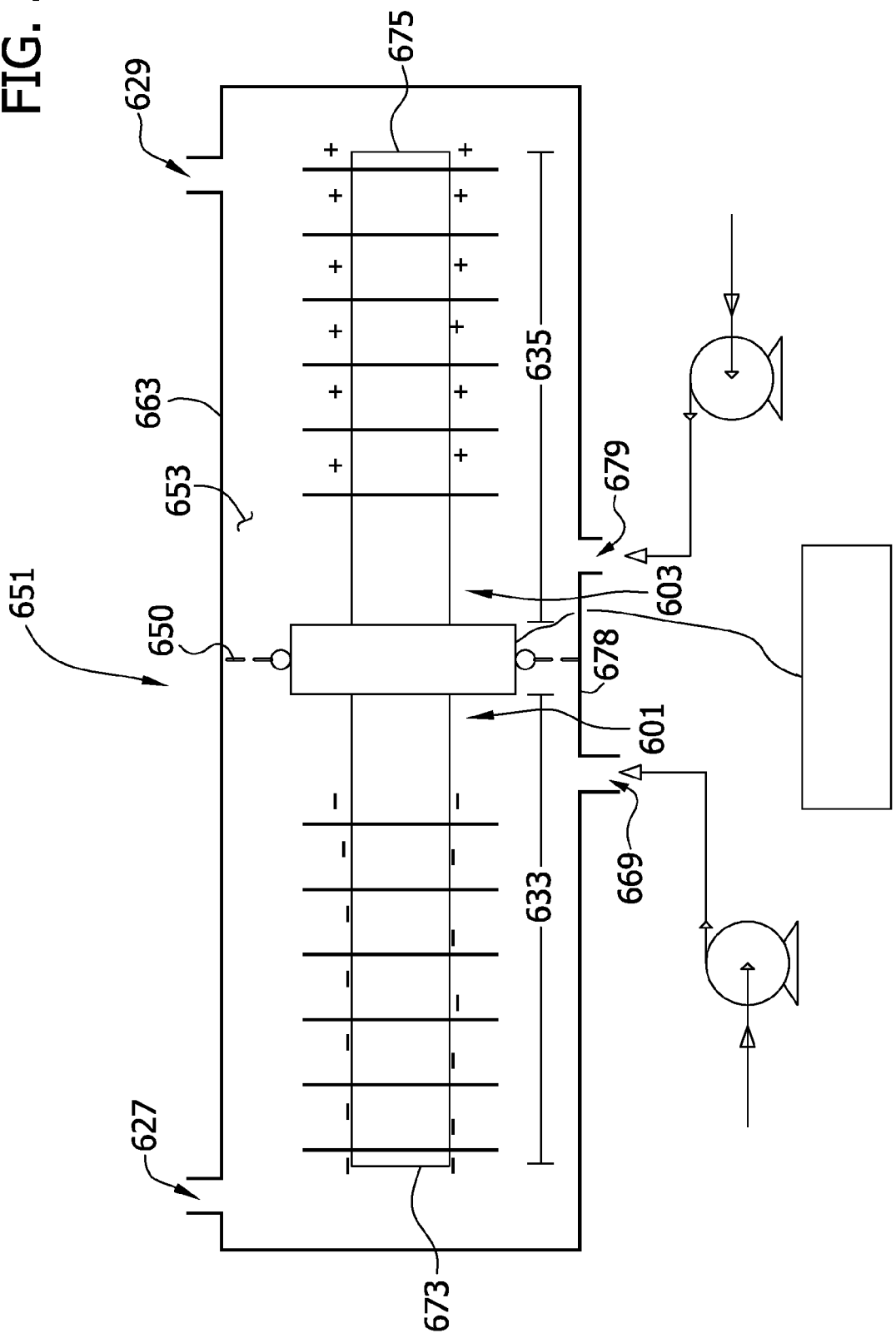
Figure 6:
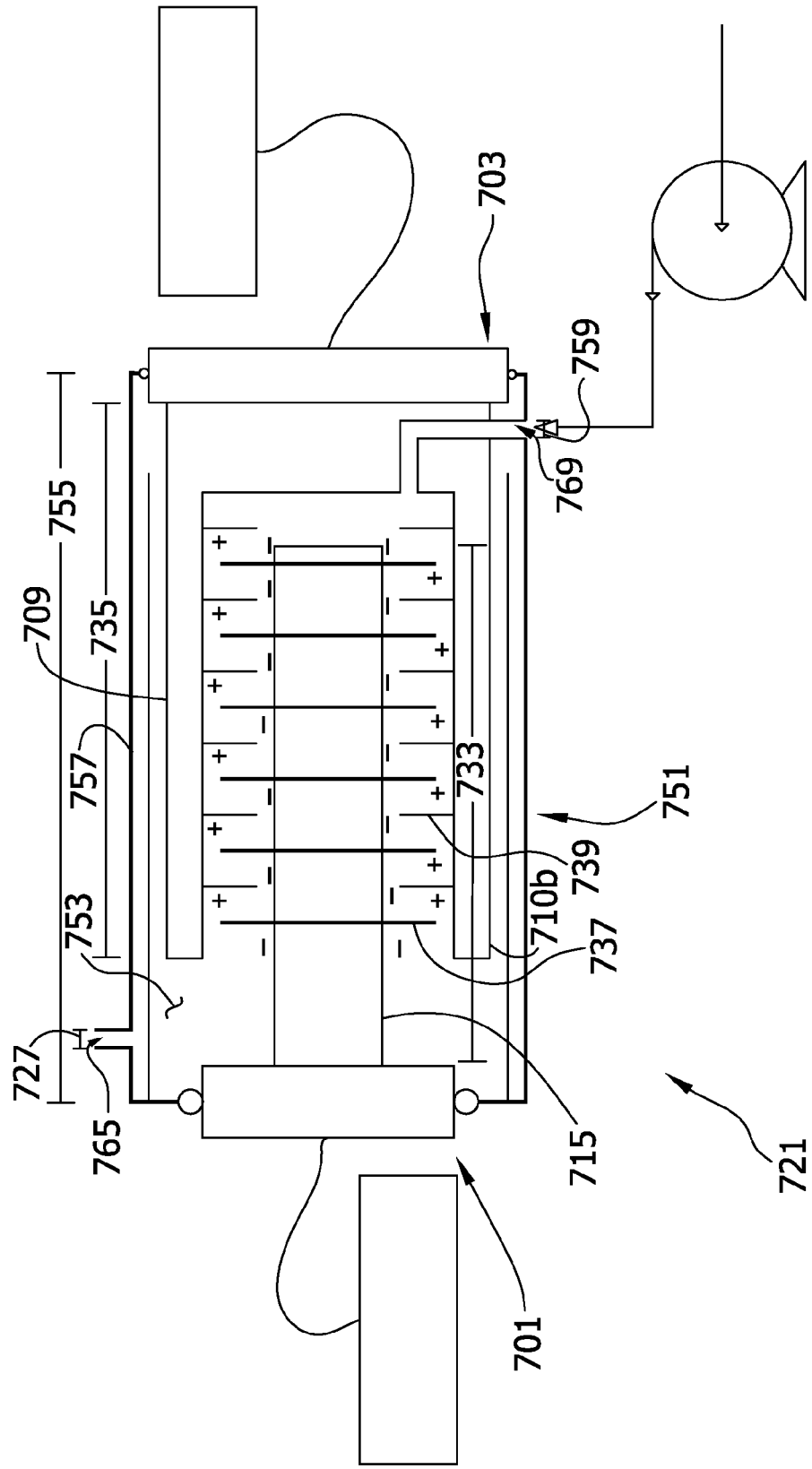

Referring back to FIG. 1, a waveguide assembly, generally indicated at 101, extends longitudinally at least in part within the interior space 153 of the chamber 121 to ultrasonically energize liquid (and any other components of the aqueous effluent) flowing through the interior space 153 of the chamber 121. In particular, the waveguide assembly 101 of the illustrated embodiment extends longitudinally from the lower or inlet end 125 of the chamber 121 up into the interior space 153 thereof to a terminal end 113 of the waveguide assembly disposed intermediate the inlet port (e.g., inlet port 159 where it is present). Although illustrated in FIGS. 1 and 2A as extending longitudinally into the interior space 153 of the chamber 121, it should be understood by one skilled in the art, and more particularly as illustrated in FIGS. 4-6, the waveguide assembly may extend laterally from a housing sidewall of the chamber, running horizontally through the interior space thereof. Typically, the waveguide assembly 101 is mounted, either directly or indirectly, to the chamber housing 151 as will be described later herein.

Still referring to FIG. 1, the waveguide assembly 101 suitably comprises an elongate horn assembly, generally indicated at 133, disposed entirely with the interior space 153 of the housing 151 intermediate the inlet port 159 and the outlet port 165 for complete submersion within the liquid being treated within the chamber 121, and more suitably, in the illustrated embodiment, it is aligned coaxially with the chamber sidewall 157. The horn assembly 133 has an outer surface 107 that together with the inner surface 167 of the sidewall 157 defines a flow path within the interior space 153 of the chamber 121 along which liquid and other components flow past the horn within the chamber (this portion of the flow path being broadly referred to herein as the ultrasonic treatment zone). The horn assembly 133 has an upper end defining a terminal end of the horn assembly (and therefore the terminal end 113 of the waveguide assembly) and a longitudinally opposite lower end 111. Although not shown, it is particularly preferable that the waveguide assembly 101 also comprises a booster coaxially aligned with and connected at an upper end thereof to the lower end 111 of the horn assembly 133. It is understood, however, that the waveguide assembly 101 may comprise only the horn assembly 133 and remain within the scope of this disclosure. It is also contemplated that the booster may be disposed entirely exterior of the chamber housing 151, with the horn assembly 133 mounted on the chamber housing 151 without departing from the scope of this disclosure.

The waveguide assembly 101, and more particularly the booster is suitably mounted on the chamber housing 151, e.g., on the tube 155 defining the chamber sidewall 157, at the upper end thereof by a mounting member (not shown) that is configured to vibrationally isolate the waveguide assembly (which vibrates ultrasonically during operation thereof) from the treatment chamber housing. That is, the mounting member inhibits the transfer of longitudinal and transverse mechanical vibration of the waveguide assembly 101 to the chamber housing 151 while maintaining the desired transverse position of the waveguide assembly (and in particular the horn assembly 133) within the interior space 153 of the chamber housing and allowing both longitudinal and transverse displacement of the horn assembly within the chamber housing. The mounting member also at least in part (e.g., along with the booster and/or lower end of the horn assembly) closes the inlet end 125 of the chamber 121. Examples of suitable mounting member configurations are illustrated and described in U.S. Pat. No. 6,676,003, the entire disclosure of which is incorporated herein by reference to the extent it is consistent herewith.

In one particularly suitable embodiment the mounting member is of single piece construction. Even more suitably the mounting member may be formed integrally with the booster (and more broadly with the waveguide assembly 101). However, it is understood that the mounting member may be constructed separate from the waveguide assembly 101 and remain within the scope of this disclosure. It is also understood that one or more components of the mounting member may be separately constructed and suitably connected or otherwise assembled together.

In one suitable embodiment the mounting member is further constructed to be generally rigid (e.g., resistant to static displacement under load) so as to hold the waveguide assembly 101 in proper alignment within the interior space 153 of the chamber 121. For example, the rigid mounting member in one embodiment may be constructed of a non-elastomeric material, more suitably metal, and even more suitably the same metal from which the booster (and more broadly the waveguide assembly 101) is constructed. The term "rigid" is not, however, intended to mean that the mounting member is incapable of dynamic flexing and/or bending in response to ultrasonic vibration of the waveguide assembly 101. In other embodiments, the rigid mounting member may be constructed of an elastomeric material that is sufficiently resistant to static displacement under load but is otherwise capable of dynamic flexing and/or bending in response to ultrasonic vibration of the waveguide assembly 101.

A suitable ultrasonic drive system 131 including at least an exciter (not shown) and a power source (not shown) is disposed exterior of the chamber 121 and operatively connected to the booster (not shown) (and more broadly to the waveguide assembly 101) to energize the waveguide assembly to mechanically vibrate ultrasonically. Examples of suitable ultrasonic drive systems 131 include a Model 20A3000 system available from Dukane Ultrasonics of St. Charles, Ill., and a Model 2000CS system available from Herrmann Ultrasonics of Schaumberg, Ill.

In one embodiment, the drive system 131 is capable of operating the waveguide assembly 101 at a frequency in the range of about 15 kHz to about 100 kHz, more suitably in the range of about 15 kHz to about 60 kHz, and even more suitably in the range of about 20 kHz to about 40 kHz. Such ultrasonic drive systems 131 are well known to those skilled in the art and need not be further described herein.

With particular reference to FIG. 1, the horn assembly 133 comprising an elongate, generally cylindrical horn 105 having an outer surface 107, and two or more (i.e., a plurality of) agitating members 137 connected to the horn and extending at least in part transversely outward from the outer surface of the horn in longitudinally spaced relationship with each other. The horn 105 is suitably sized to have a length equal to about one-half of the resonating wavelength (otherwise commonly referred to as one-half wavelength) of the horn. In one particular embodiment, the horn 105 is suitably configured to resonate in the ultrasonic frequency ranges recited previously, and most suitably at 20 kHz. For example, the horn 105 may be suitably constructed of a titanium alloy (e.g., Ti6Al4V) and sized to resonate at 20 kHz. The one-half wavelength horn 105 operating at such frequencies thus has a length (corresponding to a one-half wavelength) in the range of about 4 inches to about 6 inches, more suitably in the range of about 4.5 inches to about 5.5 inches, even more suitably in the range of about 5.0 inches to about 5.5 inches, and most suitably a length of about 5.25 inches (133.4 mm). It is understood, however, that the treatment chamber 121 may include a horn 105 sized to have any increment of one-half wavelength without departing from the scope of this disclosure.

Figure 7:
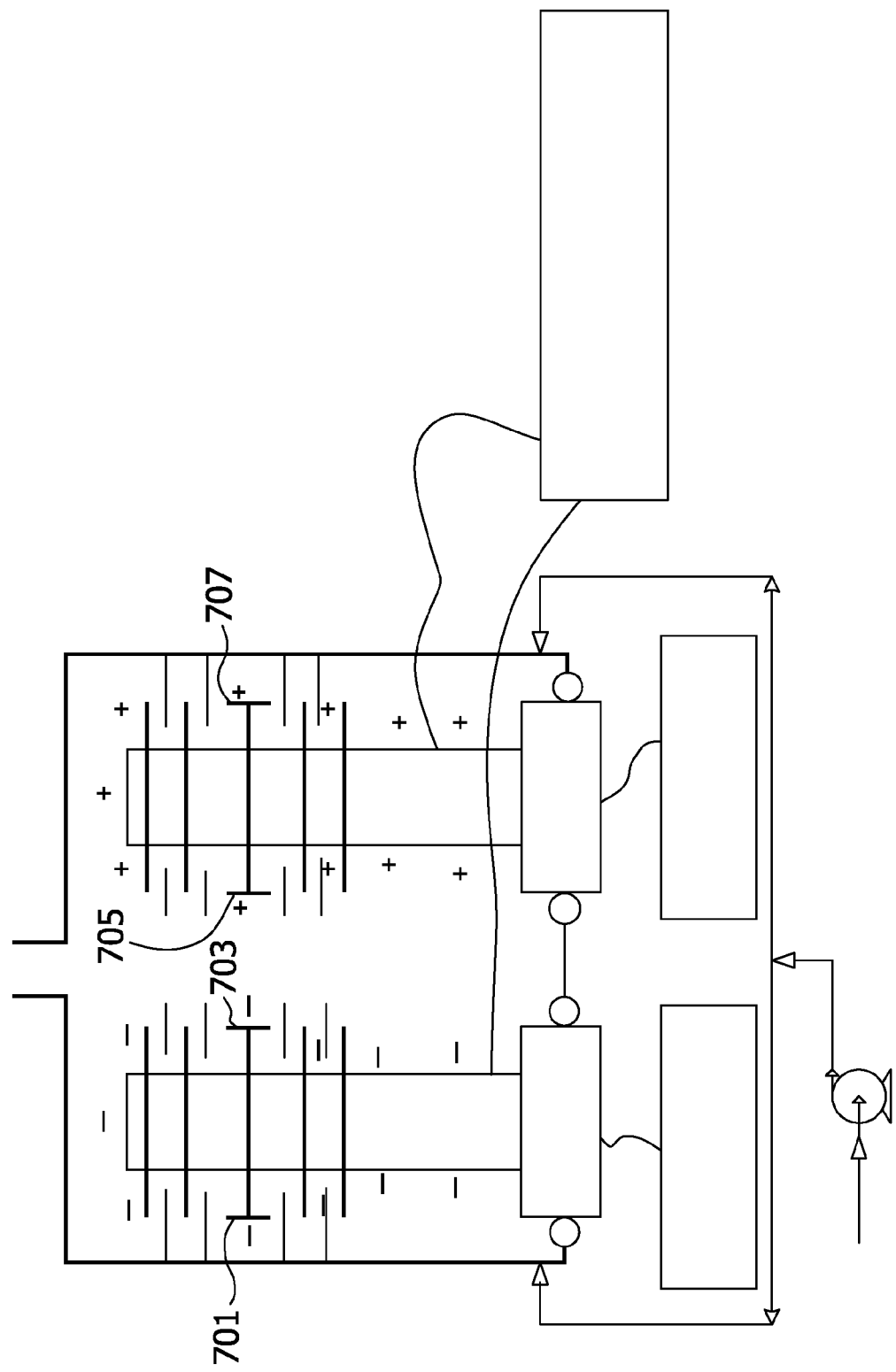

In the illustrated embodiment, the agitating members 137 comprise a series of six washer-shaped rings that extend continuously about the circumference of the horn 105 in longitudinally spaced relationship with each other and transversely (e.g., radially in the illustrated embodiment) outward from the outer surface of the horn. In this manner the vibrational displacement of each of the agitating members 137 relative to the horn 105 is relatively uniform about the circumference of the horn. It is understood, however, that the agitating members 137 need not each be continuous about the circumference of the horn 105. For example, the agitating members 137 may instead be in the form of spokes, blades, fins or other discrete structural members that extend transversely outward from the outer surface 107 of the horn 105. For example, as illustrated in FIG. 7, two of the six agitating members are in a T-shape 701, 703, 705, and 707. Specifically, the two agitating members surrounding the nodal region, as described more fully below, are in a T-shape. It has been found that members in the T-shape, generate a strong radial (e.g., horizontal) acoustic wave that further increases the cavitation effect as described more fully herein.

By way of a dimensional example, the horn assembly 133 of the illustrated embodiment of FIG. 1 has a length of about 5.25 inches (133.4 mm), one of the rings 137 is suitably disposed adjacent the terminal end 113 of the horn 105 (and hence of the waveguide assembly 101), and more suitably is longitudinally spaced approximately 0.063 inches (1.6 mm) from the terminal end of the horn 105. In other embodiments the uppermost ring 137 may be disposed at the terminal end of the horn 105 and remain within the scope of this disclosure. The rings 137 are each about 0.125 inches (3.2 mm) in thickness and are longitudinally spaced from each other (between facing surfaces of the rings) a distance of about 0.875 inches (22.2 mm).

It is understood that the number of agitating members 137 (e.g., the rings in the illustrated embodiment) may be less than or more than six without departing from the scope of this disclosure. It is also understood that the longitudinal spacing between the agitating members 137 may be other than as illustrated in FIG. 1 and described above (e.g., either closer or spaced further apart). Furthermore, while the rings 137 illustrated in FIG. 1 are equally longitudinally spaced from each other, it is alternatively contemplated that where more than two agitating members are present the spacing between longitudinally consecutive agitating members need not be uniform to remain within the scope of this disclosure. Furthermore, as illustrated in FIGS. 4-6, when the waveguide assembly extends laterally within the interior space of the chamber, the agitating members may be laterally spaced from one another.

In particular, the locations of the agitating members 137 are at least in part a function of the intended vibratory displacement of the agitating members upon vibration of the horn assembly 133. For example, in the illustrated embodiment of FIG. 1, the horn assembly 133 has a nodal region located generally longitudinally centrally of the horn 105 (e.g., between the third and fourth rings). As used herein and more particularly shown in FIG. 1, the "nodal region" of the horn 105 refers to a longitudinal region or segment of the horn member along which little (or no) longitudinal displacement occurs during ultrasonic vibration of the horn and transverse (e.g., radial in the illustrated embodiment) displacement of the horn is generally maximized. Transverse displacement of the horn assembly 133 suitably comprises transverse expansion of the horn but may also include transverse movement (e.g., bending) of the horn. Likewise, in FIGS. 4-6, in which the horn runs laterally within the interior space of the chamber housing, the "nodal region" refers to a lateral region or segment of the horn member along which little (or no) lateral displacement occurs during ultrasonic vibration of the horn and axial (e.g., longitudinal in the illustrated embodiment) displacement of the horn is generally maximized.

In the illustrated embodiment of FIG. 1, the configuration of the one-half wavelength horn 105 is such that the nodal region is particularly defined by a nodal plane (i.e., a plane transverse to the horn member at which no longitudinal displacement occurs while transverse displacement is generally maximized) is present. This plane is also sometimes referred to as a "nodal point". Accordingly, agitating members 137 (e.g., in the illustrated embodiment, the rings) that are disposed longitudinally further from the nodal region of the horn 105 will experience primarily longitudinal displacement while agitating members that are longitudinally nearer to the nodal region will experience an increased amount of transverse displacement and a decreased amount of longitudinal displacement relative to the longitudinally distal agitating members.

It is understood that the horn 105 may be configured so that the nodal region is other than centrally located longitudinally on the horn member without departing from the scope of this disclosure. It is also understood that one or more of the agitating members 137 may be longitudinally located on the horn so as to experience both longitudinal and transverse displacement relative to the horn upon ultrasonic vibration of the horn 105.

Still referring to FIG. 1, the agitating members 137 are sufficiently constructed (e.g., in material and/or dimension such as thickness and transverse length, which is the distance that the agitating member extends transversely outward from the outer surface 107 of the horn 105) to facilitate dynamic motion, and in particular dynamic flexing/bending of the agitating members in response to the ultrasonic vibration of the horn. In one particularly suitable embodiment, for a given ultrasonic frequency at which the waveguide assembly 101 is to be operated in the treatment chamber (otherwise referred to herein as the predetermined frequency of the waveguide assembly) and a particular liquid to be treated within the chamber 121, the agitating members 137 and horn 105 are suitably constructed and arranged to operate the agitating members in what is referred to herein as an ultrasonic cavitation mode at the predetermined frequency.

As used herein, the ultrasonic cavitation mode of the agitating members refers to the vibrational displacement of the agitating members sufficient to result in cavitation (i.e., the formation, growth, and implosive collapse of bubbles in a liquid) of the liquid being treated at the predetermined ultrasonic frequency. For example, where the liquid flowing within the chamber comprises an aqueous effluent, and more particularly water, and the ultrasonic frequency at which the waveguide assembly 101 is to be operated (i.e., the predetermined frequency) is about 20 kHZ, one or more of the agitating members 137 are suitably constructed to provide a vibrational displacement of at least 1.75 mils (i.e., 0.00175 inches, or 0.044 mm) to establish a cavitation mode of the agitating members. It is understood that the waveguide assembly 101 may be configured differently (e.g., in material, size, etc.) to achieve a desired cavitation mode associated with the particular liquid being treated. For example, as the viscosity of the liquid being treated changes, the cavitation mode of the agitating members may need to be changed.

In particularly suitable embodiments, the cavitation mode of the agitating members corresponds to a resonant mode of the agitating members whereby vibrational displacement of the agitating members is amplified relative to the displacement of the horn. However, it is understood that cavitation may occur without the agitating members operating in their resonant mode, or even at a vibrational displacement that is greater than the displacement of the horn, without departing from the scope of this disclosure.

In one suitable embodiment, a ratio of the transverse length of at least one and more suitably all of the agitating members to the thickness of the agitating member is in the range of about 2:1 to about 6:1. As another example, the rings each extend transversely outward from the outer surface 107 of the horn 105 a length of about 0.5 inches (12.7 mm) and the thickness of each ring is about 0.125 inches (3.2 mm), so that the ratio of transverse length to thickness of each ring is about 4:1. It is understood, however that the thickness and/or the transverse length of the agitating members may be other than that of the rings as described above without departing from the scope of this disclosure. Also, while the agitating members 137 (rings) may suitably each have the same transverse length and thickness, it is understood that the agitating members may have different thicknesses and/or transverse lengths.

In the above described embodiment, the transverse length of the agitating member also at least in part defines the size (and at least in part the direction) of the flow path along which liquid or other flowable components in the interior space of the chamber flows past the horn. For example, the horn may have a radius of about 0.875 inches (22.2 mm) and the transverse length of each ring is, as discussed above, about 0.5 inches (12.7 mm). The radius of the inner surface of the housing sidewall is approximately 1.75 inches (44.5 mm) so that the transverse spacing between each ring and the inner surface of the housing sidewall is about 0.375 inches (9.5 mm). It is contemplated that the spacing between the horn outer surface and the inner surface of the chamber sidewall and/or between the agitating members and the inner surface of the chamber sidewall may be greater or less than described above without departing from the scope of this disclosure.

In general, the horn 105 may be constructed of a metal having suitable acoustical and mechanical properties. Examples of suitable metals for construction of the horn 105 include, without limitation, aluminum, monel, titanium, stainless steel, and some alloy steels. It is also contemplated that all or part of the horn 105 may be coated with another metal such as silver, platinum, gold, palladium, lead dioxide, and copper to mention a few. In one particularly suitable embodiment, the agitating members 137 are constructed of the same material as the horn 105, and are more suitably formed integrally with the horn. In other embodiments, one or more of the agitating members 137 may instead be formed separate from the horn 105 and connected thereto.

While the agitating members 137 (e.g., the rings) illustrated in FIG. 1 are relatively flat, i.e., relatively rectangular in cross-section, it is understood that the rings may have a cross-section that is other than rectangular without departing from the scope of this disclosure. The term "cross-section" is used in this instance to refer to a cross-section taken along one transverse direction (e.g., radially in the illustrated embodiment) relative to the horn outer surface 107). Additionally, although the agitating members 137 (e.g., the rings) illustrated in FIG. 1 are constructed only to have a transverse component, it is contemplated that one or more of the agitating members may have at least one longitudinal (e.g., axial) component to take advantage of transverse vibrational displacement of the horn (e.g., at and near the nodal region of the horn illustrated in FIG. 1) during ultrasonic vibration of the waveguide assembly 101.

As best illustrated in FIG. 1, the proximal end of the horn 105 is suitably spaced longitudinally from the inlet port 125 in FIG. 1 to define what is referred to herein as a liquid intake zone in which initial swirling of liquid within the interior space 153 of the chamber housing 151 occurs upstream of the horn 105. This intake zone is particularly useful where the treatment chamber 121 is used for mixing two or more components together whereby initial mixing is facilitated by the swirling action in the intake zone as the components to be mixed enter the chamber housing 151. It is understood, though, that the proximal end of the horn 105 may be nearer to the inlet port 125 than is illustrated in FIG. 1, and may be substantially adjacent to the inlet port so as to generally omit the intake zone, without departing from the scope of this disclosure.

Now referring to FIG. 2A, a baffle assembly, generally indicated at 245 is disposed within the interior space 253 of the chamber 221, and in particular generally transversely adjacent the inner surface 267 of the sidewall 257 and in generally transversely opposed relationship with the horn 205. In one suitable embodiment, the baffle assembly 245 comprises one or more baffle members 247 disposed adjacent the inner surface 267 of the housing sidewall 257 and extending at least in part transversely inward from the inner surface of the sidewall toward the horn 205. More suitably, the one or more baffle members 247 extend transversely inward from the housing sidewall inner surface 267 to a position longitudinally intersticed with the agitating members 237 that extend outward from the outer surface 207 of the horn 205. The term "longitudinally intersticed" is used herein to mean that a longitudinal line drawn parallel to the longitudinal axis of the horn 205 passes through both the agitating members 237 and the baffle members 247. As one example, in the illustrated embodiment the baffle assembly 245 comprises five, generally annular baffle members 247 (i.e., extending continuously about the horn 205) longitudinally intersticed with the six agitating members 237. Likewise in FIGS. 4-6, when the waveguide assembly runs laterally within the housing, the one or more baffle members extend transversely inward from the housing sidewall inner surface to a position laterally intersticed with the agitating members that extend outward from the outer surface of the horn.

As a more particular example, the five annular baffle members 247 illustrated in FIG. 2A are of the same thickness as the agitating members 237 in our previous dimensional example (i.e., 0.125 inches (3.2 mm)) and are spaced longitudinally from each other (e.g., between opposed faces of consecutive baffle members) equal to the longitudinal spacing between the rings (i.e., 0.875 inches (22.2 mm)). Each of the annular baffle members 247 has a transverse length (e.g., inward of the inner surface 267 of the housing sidewall 257) of about 0.5 inches (12.7 mm) so that the innermost edges of the baffle members extend transversely inward beyond the outermost edges of the agitating members 237 (e.g., the rings). It is understood, however, that the baffle members 247 need not extend transversely inward beyond the outermost edges of the agitating members 237 of the horn 205 to remain within the scope of this disclosure.

It will be appreciated that the baffle members 247 thus extend into the flow path of liquid that flows within the interior space 253 of the chamber 221 past the horn 205 (e.g., within the ultrasonic treatment zone). As such, the baffle members 247 inhibit liquid against flowing along the inner surface 267 of the chamber sidewall 257 past the horn 205, and more suitably the baffle members facilitate the flow of liquid transversely inward toward the horn for flowing over the agitating members of the horn (and thereby, flow over the adsorbent) to thereby facilitate adsorption of the functional compounds to the adsorbent attached to the outer surface of the horn.

To inhibit gas bubbles against stagnating or otherwise building up along the inner surface 267 of the sidewall 257 and across the face on the underside of each baffle member 247, e.g., as a result of agitation of the liquid, a series of notches (broadly openings) are formed in the outer edge of each of the baffle members (not shown) to facilitate the flow of gas (e.g., gas bubbles) between the outer edges of the baffle members and the inner surface of the chamber sidewall. For example, in one particularly preferred embodiment, four such notches are formed in the outer edge of each of the baffle members in equally spaced relationship with each other. It is understood that openings may be formed in the baffle members other than at the outer edges where the baffle members abut the housing, and remain within the scope of this disclosure. It is also understood, that these notches may number more or less than four, as discussed above, and may even be completely omitted.

It is further contemplated that the baffle members 247 need not be annular or otherwise extend continuously about the horn 205. For example, the baffle members 247 may extend discontinuously about the horn 205, such as in the form of spokes, bumps, segments or other discrete structural formations that extend transversely inward from adjacent the inner surface 267 of the housing sidewall 257. The term "continuously" in reference to the baffle members 247 extending continuously about the horn does not exclude a baffle member as being two or more arcuate segments arranged in end-to-end abutting relationship, i.e., as long as no significant gap is formed between such segments. Suitable baffle member configurations are disclosed in U.S. application Ser. No. 11/530,311 (filed Sep. 8, 2006), which is hereby incorporated by reference to the extent it is consistent herewith.

Also, while the baffle members 247 illustrated in FIG. 2A are each generally flat, e.g., having a generally thin rectangular cross-section, it is contemplated that one or more of the baffle members may each be other than generally flat or rectangular in cross-section to further facilitate the flow of gas bubbles along the interior space 253 of the chamber 221. The term "cross-section" is used in this instance to refer to a cross-section taken along one transverse direction (e.g., radially in the illustrated embodiment, relative to the horn outer surface 207).

Referring back again to FIG. 1, the treatment chamber 121 is further connected to an electrical conducting generator, such as a DC current generator (indicated at 120), for creating an electrical potential within the interior space 153 of the chamber housing 151. It has been found that when mixing liquids such as in many electrochemical reactions, there is the disadvantage that arises from the fact that electrochemical reactions are heterogeneous and take place at the electrode-electrolyte interface in electrochemical reactors. Therefore, the performance of the electrochemical reactor often suffers from mass-transport limitations and the size of the specific electrode area. Specifically, one of the main factors that control the rate of a chemical reaction is the rate at which the reactants come together. During normal electrochemical reactions, there is little if any agitation supplied to the system and, as such, the diffusion rate of the reactants to the respective electrodes to facilitate a reaction is low. By electrically charging the treatment chamber of the present disclosure, these disadvantages can be overcome. Specifically, the application of the ultrasonic horn to also act as an electrode will supply the necessary agitation to the reaction mass. When the horn is operating in the cavitation mode, microcurrents that are generated, as discussed above, will minimize and, more desirably, eliminate the hydrodynamic boundary layer around the electrode-like horn. Furthermore, the microcurrents will supply motion to the chemical reactants and the reaction products, which can significantly enhance the overall chemical reactions that occur at the electrode.

As illustrated in FIG. 1, the generator 120 can be connected to the chamber 121 through electrical wires (indicated at 122 and 124) to one or more components of the treatment chamber 121. Specifically, in the illustrated embodiment, electrical wires 122 and 124 electrically connect the DC current generator 120 to the terminal end of the horn 105 (e.g., the terminal end 113 of the waveguide assembly 101) and the sidewall 157 of the chamber housing 151, respectively. Depending upon the materials used to form each of the sidewall of the chamber housing and the horn of the waveguide assembly, the electrical current produced creates an electrode potential such that the sidewall of the chamber housing shows properties typical of an anode and the horn shows the properties of a cathode, or vice versa.

Typically, the electrode potential produced by the generator 120 of the present disclosure is in the range of from about 0.1V to about 15V. More suitably, the electrode potential is in the range of from about 0.5V to about 5.0V and, more suitably, from about 1.0V to about 3.0V. Furthermore, typical current density produced by the electrode potential within the treatment chamber ranges from about 0.1 $kA/m^2$ to about 2 $kA/m^2$ and, more suitably, the current density can be from about 1 $kA/m^2$ to about 1.5 $kA/m^2$.

More specifically, the electrode potential will be determined and produced in an amount required for the desired purpose of treatment chamber. For example, where the treatment chamber is desired for use in attaching a negatively charged functional compound from the aqueous effluent, the electrode potential produced will be that which is necessary to produce a positively charged adsorbent on the outer surface of the horn (e.g., anode). Likewise, when the chamber is designed for use in attaching a positively charged functional compound from the aqueous effluent, the electrode potential produced will be that which is necessary to produce a less positively charged or negatively charged adsorbent on the outer surface of the horn (e.g., cathode). It should be understood by one skilled in the art that the examples described above should not be limiting as the electrode potential can be controlled over various ranges and for other additional uses without departing from the scope of this disclosure.

Moreover, it should be understood by one skilled in the art, that while the generator 120 is connected to the sidewall 157 and the terminal end 119 of the horn 105 in FIG. 1, the generator can be connected to numerous other areas of the treatment chamber 21 without departing from the scope of this disclosure. Specifically, as illustrated in FIGS. 2A and 3-6 and described more fully below, the electrical wires can connect the generator to multiple waveguide assemblies, each being fully disposed within the interior of the chamber housing of a single treatment chamber. More particularly, as illustrated in FIGS. 2A and 3-6, there are two waveguide assemblies, each having their own corresponding horns, in which the electrical wires connect the generator to each horn, thereby creating a cathode-like effect on the adsorbent located on the outer surface of the first horn and an anode-like effect on the adsorbent located on the outer surface of the second horn. It should be understood that the electrode potential could alternatively electrically charge the adsorbent located on the outer surface of the first horn as an anode and the adsorbent located on the outer surface of the second horn as a cathode without departing from the scope of this disclosure.

Referring again to FIG. 1, as there is an electrode potential produced within the interior 153 of the chamber housing 151 by connecting the sidewall 157 of the housing 151 and the outer surface 107 of the horn 105 to a generator 120, it is desirable for the housing 151 to be electrically insulated from the waveguide assembly 101 to maintain the electrode-like effect. As such, in the illustrated embodiment, the housing sidewall 157 is separated from the waveguide assembly 101 (and thus, the horn 105) by at least two insulating members 10 and 12.

Typically, the insulating members 10, 12 can be made using any insulating material known in the art. For example, the insulating members 10, 12 may be produced using any one of a multitude of known inorganic or organic insulating materials. Particularly suitable materials that could be used for the insulating members 10, 12 include solid materials with a high dielectric strength, such as for example, glass, mylar, kapton, ceramic, phenolic glass/epoxy laminates, and the like.

After the compounds have been adsorbed to the energized and electrically charged adsorbent, the liquid, containing the produced carrier component, is exhausted from the treatment chamber 121 through at least one outlet end 127. The outlet end 127 is capable of letting the liquid escape from the chamber 121, while providing enough flow resistance to keep the pressure within the chamber 121 at a suitable level. Typically, the pressure within the chamber 121 is maintained within a range of from about 1 pound/square inch (psi) to about 10 psi. While the illustrated embodiment of FIG. 1 depicts a treatment chamber 121 having only one outlet port 165 in the outlet end 127, it should be understood that the treatment chamber used in the processes of the present disclosure can suitably contain more than one inlet port and inlet end without departing from the scope of this disclosure.

Once the carrier component of the delivery system is produced, the carrier component is contacted with a substrate. In one embodiment, examples of substrates that will benefit from the functional compounds delivered by the delivery system include substrates such as woven and non-woven materials made from a polyolefin polymer such as polypropylene, polyethylene, polyester, and the like. These substrates are then used in products such as child care articles, face mask fabrics, air filtration fabrics, medical gowns, medical drapes, wipes, hand towels, facial tissue, bath tissue, transdermal delivery devices, wound dressings, automobile covers, boat covers, and deck furniture.

Although not needed, in some embodiments, it may be desirable to pre-treat or post-treat the polymeric substrates which may further serve to affix the carrier component of the delivery system to the materials. For example, substrates made from synthetic polymers can undergo a pretreatment process for increasing the negative surface charge. In one embodiment, such pretreatment processes include subjecting the substrate to a corona treatment or to an electret treatment. An electret treatment, for example, is disclosed in U.S. Pat. No. 5,964,926 issued to Cohen, which is incorporated herein by reference in its entirety. Such pretreatments have been found not only to increase the negative surface charge of polymeric materials, but also assist in wetting out the polymer and enhancing surface adhesion between the polymer and the carrier component of the delivery system of the present disclosure.

In addition to pretreatment processes, substrates contacted with the carrier components can also undergo various post treatment processes which further serve to affix the components to the substrate. For example, once the carrier component has been contacted with the substrates, the substrates can be subjected to radio frequency radiation or to microwave radiation. Adsorbents, such as alumina, are known to adsorb radio frequency and microwave radiation causing the carrier components to heat. Once heated, it is believed that the components become further embedded into the polymeric substrate. Further, the particles can be heated without also heating the substrate to higher than desired temperatures.

In another embodiment, the substrate is the skin of a patient. Specifically, the carrier component can be combined with a lotion or formulation for transdermal use. For example, the carrier component can contain a UV absorber and be combined with a skin care formulation to be used as a sunscreen lotion or sunblock.

In yet another embodiment, the substrate is tissue inside of the body of a patient, such as an organ or muscle. In such embodiments, the carrier component can be administered to the patient orally, parenterally, intraperitoneally, intravenously, or intradermally. In one particular embodiment, the carrier component of the delivery system can be used with capsules, tablets, pills, powders, and granules for oral administration. In such solid dosage forms, the carrier components are ordinarily combined with one or more adjuvants appropriate to the indicated route of administration. If administered in capsules or tablets, the carrier components can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and or polyvinyl alcohol, and then tableted or encapsulated for convenient administration. Such capsules or tablets can contain a controlled-release formulation such as can be provided in a dispersion of the carrier component in hydroxypropylmethyl cellulose. In the case of capsules, tablets, and pills, the delivery systems can also comprise buffering agents such as sodium citrate, or magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such delivery systems can also comprise adjuvants, such as wetting agents, emulsifying and suspending agents, and sweetening, flavoring, and perfuming agents.

In another embodiment, the delivery systems containing the carrier components can be injected into the patient for the purpose of delivering the functional compounds. Depending upon the carrier component used, the component can be contacted with the patient parenterally, intraperitoneally, intratumor, or intrapleural. The term parental as used herein includes subcutaneous, intravenous, intramuscular, or intrasternal injection, or infusion technique.

Injectable delivery system preparations, for example sterile injectable aqueous or oleaginous suspensions, can be formulated according to the known art using suitable dispersing or wetting agents and suspending agents. Among the acceptable vehicles that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can also be used. Mixtures of solvents and wetting agents discussed herein are also useful.

In one specific injectable embodiment, the delivery system is administered parentally. Formulations for parenteral administration can be in the form of aqueous or non-aqueous isotonic sterile injection solutions or suspensions. These solutions and suspensions can be prepared from sterile powders or granules having one or more of the diluents mentioned for the use in the formulations for oral administration. The carrier components can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Additionally, as noted above, the bound functional compound in the delivery system can be used with or without a triggerable release. In one embodiment, the functional compounds can be selectively released by an environmentally created pH trigger, such as by either a basic or acidic environmental condition. For example, the functional compound can be an antifungal compound that is released in the basic/alkaline environment of a vagina with a yeast infection. In another example, the functional compound is an anti-microbial to treat an infection in the basic environment of the small intestine after it has passed through the acidic environment of the stomach.

Other triggering mechanisms can suitably include exposure to changes in temperature, moisture, chemical stimuli, body exudates, and combinations thereof.

As further noted above, in some embodiments, the treatment chamber can include more than one waveguide assembly having at least two horn assemblies for ultrasonically treating and electrically charging adsorbent. Referring to FIG. 2A, the treatment chamber 221 comprises a housing 251 defining an interior space 253 of the chamber 221 through which liquid is delivered from two laterally opposing inlet ends 269 and 279. The housing 251 comprises an elongate tube 255 defining, at least in part, a sidewall 257 of the chamber 221. The tube 255 has two inlet ports 240 and 245 formed therein and being laterally opposed to one another through which one or more functional compounds in an aqueous effluent to be adsorbed within the chamber 221 are delivered to the interior space 253 thereof, and at least one outlet port 265 through which the liquid, once treated, exits the chamber 221.

Two waveguide assemblies 201 and 203 extend longitudinally at least in part within the interior space 253 of the chamber 221 to ultrasonically energize adsorbent located within the interior space 253 of the chamber 221. Each waveguide assembly 201 and 203 separately includes an elongate horn assembly, generally indicated at 233 and 235, respectively, each disposed entirely within the interior space 253 of the housing 251 intermediate the inlet ports 269 and 279 and the outlet port 265 for complete submersion within the liquid within the chamber 221. Each horn assembly 233 and 235 can be independently constructed as described (including the horns 205 and 209, along with the plurality of agitating members 237 and 239 and baffle assemblies 245 and 249) for the single horn assembly configuration of FIG. 1 above.

Figure 2B:
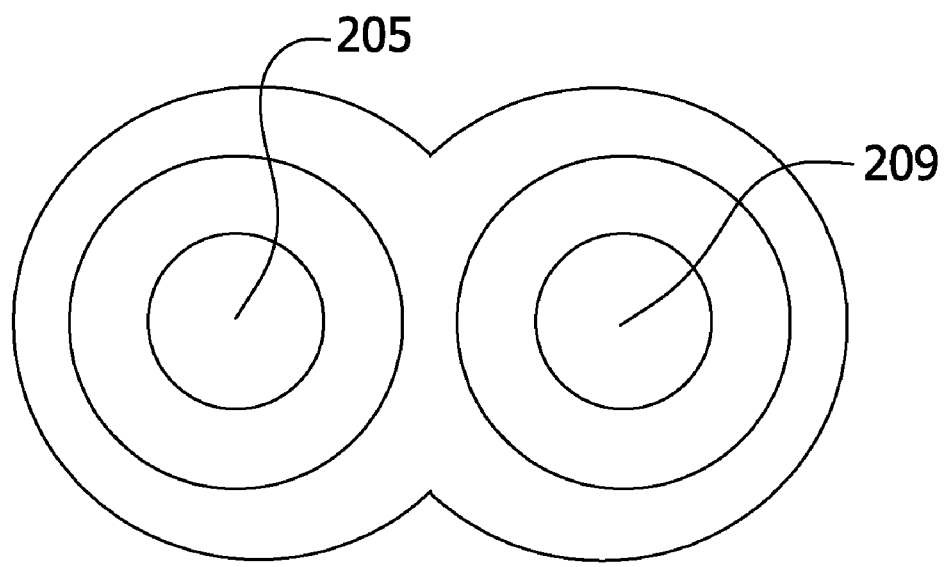

Still referring to FIG. 2A, a generator (not shown) can be electrically connected to the outside surfaces 207 and 211 of horns 205 and 209, respectively, of the two horn assemblies 233 and 235 to create an electrode potential within the interior 253 of the housing 251 of the chamber 221. As illustrated in FIG. 2A, the adsorbent (not shown) located on the outer surface 211 of the second horn 209 is electrically charged as an anode, while the adsorbent (not shown) located on the outer surface 207 of the first horn 205 is electrically charged as a cathode (see also FIG. 2B, illustrating the terminal end of the first horn 205 as a cathode and the terminal end of the second horn 209 as an anode). It should be understood that the outer surface of the first horn 205 (and the adsorbent located thereon) could alternatively act as the anode and the outer surface of the second horn 209 (and the adsorbent located thereon) could act as the cathode without departing from the scope of this disclosure. Furthermore, as with the treatment chamber of FIG. 1, the housing 251 is separated from the first waveguide assembly 201 using at least a first insulating member 210 and at least a second insulating member 212 and from the second waveguide assembly 203 using at least a third insulating member 214 and at least a fourth insulating member 216.

Figure 3:
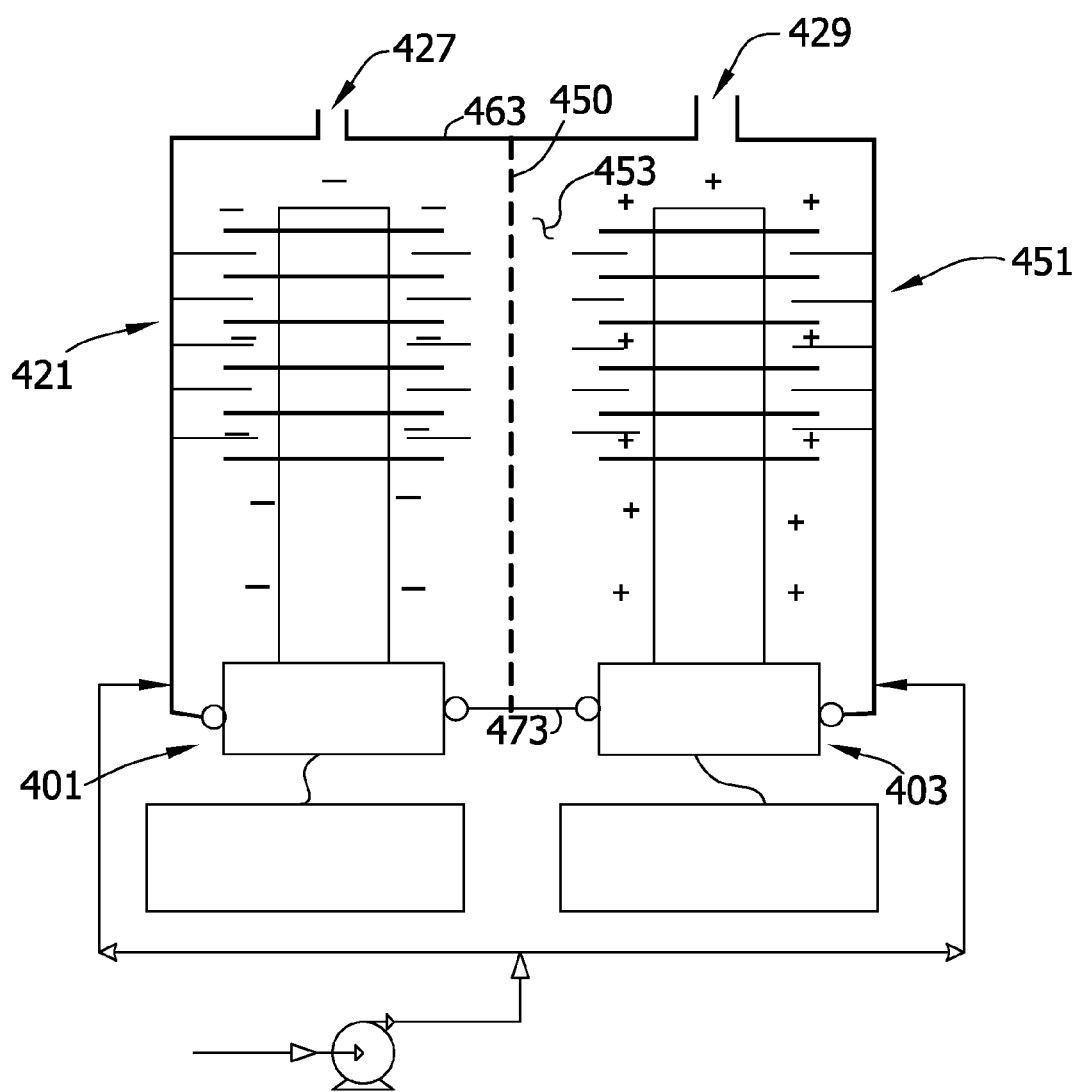

Now referring to FIG. 3, the treatment chamber 421 is similar to the treatment chamber 221 of FIG. 2A in that the chamber 421 contains two separate waveguide assemblies 401 and 403. The waveguide assemblies 401, 403 of FIG. 3, however, are further separated within the interior space 453 of the housing 451 by a mesh substrate 450 that runs laterally between the first waveguide assembly 401 and the second waveguide assembly 403. More particularly, the mesh substrate 450 extends from the upper longitudinal end (e.g., first longitudinal end) of the housing, generally indicated at 463 (e.g., corresponding to closure 263 of FIG. 2A) to the lower longitudinal end (e.g., second longitudinal end) of the housing, generally indicated at 473. The mesh substrate is generally capable of separating gases being generated as compounds are electrolyzed from the liquid. For example, in the electrolysis of ammonia, nitrogen gas is formed at the anode and hydrogen gas is formed at the cathode. It is desirable to keep these gases separate for later resale purposes.

Furthermore, the mesh substrate can be used to allow formed ions to migrate across the treatment chamber from the anode to the cathode so as to keep ionic neutrality in the entire liquid. For example, the electrolysis of water forms hydrogen gas and oxygen gas. At the anode, oxygen gas is formed along with the hydrogen ion ($H^+$) and, at the cathode, hydrogen gas is formed along with the hydroxyl ion ($OH^-$). Both the hydrogen and hydroxyl ions can migrate across this mesh substrate so as to maintain ionic neutrality within the interior of the treatment chamber.

Typically, the mesh substrate can be made of any suitable material known in the art. For example, one particular material for the mesh substrate is stainless steel. Further examples include, mesh substrates made from polyethylene, polypropylene, and perfluorinated materials. Suitably, the mesh substrate has a pore size of from about 15 microns to about 450 microns and, more suitably, from about 20 microns to about 100 microns. The mesh substrate typically has a thickness of from about 0.001 inches to a bout 0.05 inches and, more suitably, from about 0.005 inches to about 0.04 inches.

As the treatment chamber 421 is divided into two compartments by the mesh substrate 450, it is suitable for the housing 451 to include more than one outlet port. Specifically, in the illustrated embodiment, there are two outlet ports 427 and 429. More specifically, the first outlet port 427 allows liquid that has had functional compounds removed and adsorbed by the adsorbent located on the first waveguide assembly 401 to exit the interior space 453 of the chamber housing 451, and the second outlet port 429 allows liquid that has had functional compounds removed and adsorbed by the adsorbent located on the second waveguide assembly 403 to exit the interior space 453 of the chamber housing 451. It should be understood by one skilled in the art that, while FIG. 3 depicts two outlet ports, the housing 451 of the treatment chamber 421 may include more than two outlet ports, or alternatively only one outlet port, without departing from the scope of this disclosure.

Referring now to FIG. 4, the treatment chamber 521 is generally elongate, however, in contrast to FIGS. 1-3, the treatment chamber 521 is configured such that fluid enters the chamber 521 at the inlet end 535 thereof, flows generally laterally within the chamber (e.g., toward the right in the orientation of illustrated embodiment) and exits the chamber 521 generally at the outlet end 527 of the chamber 521. The treatment chamber 521 comprises a housing 551 defining an interior space 553 of the chamber 521 through which liquid is delivered from at least one inlet port 569. The housing 551 comprises an elongate tube 555 defining, at least in part, a sidewall 557 of the chamber 521. The housing 551 has two longitudinally opposing ends through which one or more aqueous effluents having functional compounds to be adsorbed by the adsorbent within the chamber 521 are delivered to the interior space 553 thereof, and at least one outlet port 565 through which the liquid, once the functional compounds have been adsorbed, exits the chamber 521.

Two waveguide assemblies 501 and 503 extend laterally at least in part within the interior space 553 of the chamber 521 to ultrasonically energize and electrically charge adsorbent within the interior space 553 of the chamber 521. Each waveguide assembly 501 and 503 separately includes an elongate horn assembly, generally indicated at 533 and 535, respectively, each disposed entirely within the interior space 553 of the housing 551 intermediate the inlet port 569 and the outlet port 565 for complete submersion within the liquid within the chamber 521. In the illustrated embodiment, the terminal ends 573 and 575 of horn assemblies 533 and 535, respectively, directly face towards each other. Each horn assembly 533 and 535 can be independently constructed as described (including the horns 505 and 509, along with the plurality of agitating members 537 and 539 and baffle assemblies (not shown)) for the single horn assembly configuration of FIG. 1 above.

Still referring to FIG. 4, an electric DC current generator (not shown) can be electrically connected to the outside surfaces 507 and 511 of horns 505 and 509, respectively, of the two horn assemblies 533 and 535 to create an electrode potential within the interior space 553 of the housing 551 of the chamber 521. As illustrated in FIG. 4, the outer surface 511 of the second horn 509 (and the adsorbent located thereon (not shown)) is electrically charged as an anode, while the outer surface 507 of the first horn 505 (and the adsorbent located thereon (not shown)) is electrically charged as a cathode. It should be understood that the outer surface of the first horn 505 (and adsorbent located thereon (not shown)) could be alternatively electrically charged as the anode and the outer surface of the second horn 509 (and adsorbent located thereon (not shown)) could be charged as the cathode without departing from the scope of this disclosure. Furthermore, as with the treatment chamber of FIGS. 1 and 2A, the housing 551 is separated from the first waveguide assembly 501 using at least a first insulating member 510 and at least a second insulating member 512 and from the second waveguide assembly 503 using at least a third insulating member 514 and at least a fourth insulating member 516.

As illustrated in FIG. 5, in some embodiments in which two or more waveguide assemblies 601 and 603 extend laterally at least in part within the interior space 653 of the chamber 621 to ultrasonically energize and electrically charge adsorbent within the interior space 653 of the chamber 621, the terminal ends 673 and 675 of horn assemblies 633 and 635, respectively, face away from each other.

In the illustrated embodiment, the waveguide assemblies 633 and 635 are separated within the interior space 653 of the housing 651 by a mesh substrate 650, similar to the mesh substrate of FIG. 3, that runs laterally between the first waveguide assembly 601 and the second waveguide assembly 603. More particularly, the mesh substrate 650 extends from the upper longitudinal end (e.g., first longitudinal end) of the housing, generally indicated at 663 (e.g., corresponding to closure 263 of FIG. 2A) to the lower longitudinal end (e.g., 2nd longitudinal end) of the housing, generally indicated at 678. In the illustrated embodiment, the mesh substrate 650 provides structural support to the first waveguide assembly 601 and second waveguide assembly 603, and more particularly, is constructed to substantially vibrationally isolate the first waveguide assembly 601 and second waveguide assembly 603 within the interior space 653 from the chamber housing 651.

Like the waveguide assembly of FIG. 1 described above, the first waveguide assembly 601 and the second waveguide assembly 603 can suitably be mounted on the mesh substrate 650 by a mounting member (not shown). The mounting member used as described above for the illustrated embodiment of FIG. 1 can be used as the mounting member in this embodiment.

As the treatment chamber 621 is divided into two compartments by the mesh substrate 650, it is suitable for the housing 651 to include more than one inlet port (as illustrated, the housing includes a first inlet port, generally indicated at 669, and a second inlet port, generally indicated at 679) and more than one outlet port (as illustrated, the housing includes a first outlet port, generally indicated at 627, and a second outlet port, generally indicated at 629). More specifically, the first inlet port 669 allows one or more liquid solutions having functional compounds to enter into the interior space 653 of the chamber housing 651 to be adsorbed by adsorbent located on the first waveguide assembly 601 and then the first outlet port 627 allows liquid that has had functional compounds removed and adsorbed by the adsorbent located on the first waveguide assembly 601 to exit the interior space 653 of the chamber housing 651, and the second inlet port 679 allows one or more liquid solutions having functional compounds to enter into the interior space 653 of the chamber housing 651 to be adsorbed by the adsorbent located on the second waveguide assembly 603 and then the second outlet port 629 allows liquid that has had functional compounds removed and adsorbed by adsorbent located on the second waveguide assembly 603 to exit the interior space 653 of the chamber housing 651.

In yet another alternate configuration, as illustrated in FIG. 6, the treatment chamber 721 is generally elongate and configured such that fluid enters the chamber 721 at the inlet end 759 thereof, flows generally laterally within the chamber (e.g., toward the left in the orientation of illustrated embodiment) and exits the chamber 721 generally at the outlet end 727 of the chamber 721. The treatment chamber 721 comprises a housing 751 defining an interior space 753 of the chamber 721 through which liquid is delivered from at least one inlet port 769. The housing 751 comprises an elongate tube 755 defining, at least in part, a sidewall 757 of the chamber 721. The housing 751 has two longitudinally opposing ends through which one or more liquid solutions having functional compounds to be adsorbed within the chamber 721 are delivered to the interior space 753 thereof, and at least one outlet port 765 through which the liquid exits the chamber 721.

Two waveguide assemblies 701 and 703 extend laterally at least in part within the interior space 753 of the chamber 721 to ultrasonically energize and electrically charge adsorbent within the interior space 753 of the chamber 721. Each waveguide assembly 701 and 703 separately includes an elongate horn assembly, generally indicated at 733 and 735, respectively, each disposed entirely within the interior space 753 of the housing 751 intermediate the inlet port 769 and the outlet port 765 for complete submersion within the liquid within the chamber 721. In the illustrated embodiment, the second horn, indicated generally at 709, of second horn assembly 735 of the second waveguide assembly 703 is configured in a hollow cylinder shape. The first horn member, indicated at 715, of the first horn assembly 733 of the first waveguide assembly 701 is disposed lengthwise within the hollow cylinder shaped second horn 709.

In an alternative embodiment (not shown), the second horn can be configured in a U-shape and includes two arm members. The first horn member of the first horn assembly of the first waveguide assembly is disposed between the first arm member and the second arm member of the second horn. When the first horn and the second horn members each comprise agitating members as described above, this configuration can allow for better overlap of the agitating members, producing increased cavitation.

In either of the above two embodiments, each horn assembly 733 and 735 can further include the plurality of agitating members 737 and 739, respectively, and baffle assemblies (not shown) as with the single horn assembly configuration of FIG. 1 above.

Figure 8:
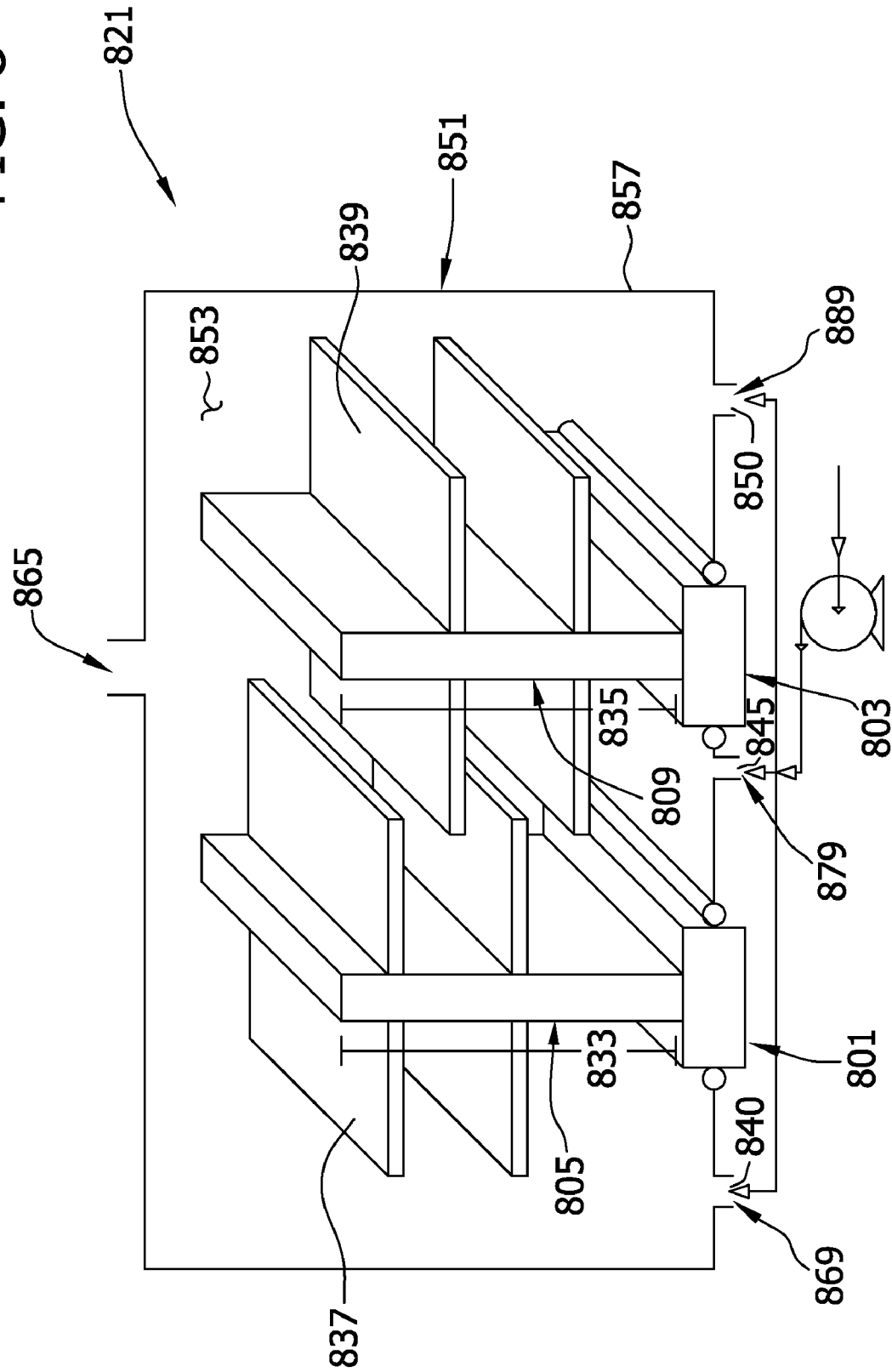

Now referring to FIG. 8, the treatment chamber 821 comprises a housing 851 defining an interior space 853 of the chamber 821 through which liquid is delivered from three laterally aligned inlet ends 869, 879 and 889. The housing 851 comprises an elongate tube defining, at least in part, a sidewall 857 of the chamber 821. The tube has three inlet ports 840, 845 and 850 formed therein and being laterally aligned to one another through which one or more liquid solutions or components to be treated within the chamber 821 are delivered to the interior space 853 thereof, and at least one outlet port 865 through which the liquid, once treated, exits the chamber 821.

Two waveguide assemblies 801 and 803 extend longitudinally at least in part within the interior space 853 of the chamber 821 to ultrasonically energize liquid flowing through the interior space 853 of the chamber 821. Each waveguide assembly 801 and 803 separately includes a plate-like elongate horn assembly, generally indicated at 833 and 835, respectively, each disposed entirely within the interior space 853 of the housing 851 intermediate the inlet ports 869, 879 and 889 and the outlet port 865 for complete submersion within the liquid being treated within the chamber 821. Each horn assembly 833 and 835 can be independently constructed as described (including the horns 805 and 809, along with the plurality of agitating members 837 and 839 and baffle assemblies (not shown)) for the single horn assembly configuration of FIG. 1 above. In this configuration, the agitating members 837 and 839, when present, are flat disk-like pieces that surround the outer surface of the plate-like horn members.

Furthermore, in the treatment chamber illustrated in FIG. 8, a generator (not shown) can be electrically connected to the outside surfaces of horns 805 and 809 as discussed of the treatment chamber in FIG. 2A above.

In view of the above, it will be seen that the several objects of the disclosure are achieved and other advantageous results obtained.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the disclosure, it is intended that all matter contained in the above description and shown in the accompanying drawings shall be interpreted as illustrative and not in a limiting sense.

What is claimed is:

1. A process of delivering functional compounds to a substrate, the process comprising:

introducing an aqueous effluent comprising at least one functional compound through at least one inlet port of an elongate housing of a treatment chamber, the housing comprising longitudinally opposite ends and an interior space, the housing further being generally closed at at least one longitudinal end, and wherein the housing comprises an adsorbent located within the interior space;

ultrasonically energizing and electrically charging the adsorbent at a predetermined ultrasonic frequency and electrode potential within the housing using an electrically-charged elongate ultrasonic waveguide assembly, the waveguide assembly comprising an elongate ultrasonic horn;

adsorbing the functional compound to the surface of the energized and electrically charged adsorbent to form a carrier component of a delivery system;

exhausting the carrier component from at least one outlet port of the housing; and contacting the carrier component with a substrate.

2. The process as set forth in claim 1 wherein the ultrasonic horn is disposed at least in part intermediate the inlet port and the outlet port of the housing and has an outer surface, wherein the adsorbent is located on the outer surface of the ultrasonic horn for contact with the aqueous effluent flowing within the housing from the inlet port to the outlet port.

3. The process as set forth in claim 2 wherein the electrode potential is produced by electrically contacting both the housing and the ultrasonic horn with an electrical current source.

4. The process as set forth in claim 3 wherein the electrode potential produced is in the range of 0.1V to about 15V.

5. The process as set forth in claim 1 wherein the ultrasonic horn further comprises a plurality of discrete agitating members in contact with and extending transversely outward from the outer surface of the horn intermediate the inlet port and the outlet port of the housing in longitudinally spaced relationship with each other, the agitating members and the ultrasonic horn being constructed and arranged for dynamic motion of the agitating members relative to the ultrasonic horn upon ultrasonic vibration of the ultrasonic horn at the predetermined frequency and to operate in an ultrasonic cavitation mode of the agitating members corresponding to the predetermined frequency.

6. A process of delivering functional compounds to a substrate, the process comprising:

introducing an aqueous effluent comprising at least one functional compound through at least one inlet port of an elongate housing of a treatment chamber, the housing comprising longitudinally opposite ends and an interior space, the housing further being generally closed at at least one longitudinal end, and wherein the housing comprises an adsorbent located within the interior space;

ultrasonically energizing and electrically charging the adsorbent at a predetermined ultrasonic frequency and electrode potential within the housing using a first electrically-charged longitudinally elongate ultrasonic waveguide assembly and a second electrically-charged longitudinally elongate ultrasonic waveguide assembly, wherein the first waveguide assembly and the second waveguide assembly are oriented in parallel within the housing, the first waveguide assembly comprising a first elongate ultrasonic horn and the second waveguide assembly comprising a second elongate ultrasonic horn;

adsorbing the functional compound to the surface of the energized and electrically charged adsorbent to form a carrier component of a delivery system;

exhausting the carrier component from at least one outlet port of the housing; and contacting the carrier component with a substrate.

7. The process as set forth in claim 6 wherein the first ultrasonic horn and the second ultrasonic horn are independently disposed at least in part intermediate the inlet port and the outlet port of the housing and each independently have an outer surface, wherein the adsorbent is located on the outer surface of at least one of the first ultrasonic horn and second ultrasonic horn for contact with the aqueous effluent flowing within the housing from the inlet port to the outlet port.

8. The process as set forth in claim 7 wherein the electrode potential is produced by electrically contacting both the first ultrasonic horn and the second ultrasonic horn with an electrical current source.

9. The process as set forth in claim 8 wherein the electrode potential produced is in the range of 0.1V to about 15V.

10. The process as set forth in claim 6 wherein the first ultrasonic horn further comprises a plurality of discrete agitating members in contact with and extending transversely outward from the outer surface of the first ultrasonic horn intermediate the inlet port and the outlet port of the housing in longitudinally spaced relationship with each other, the agitating members and the first ultrasonic horn being constructed and arranged for dynamic motion of the agitating members relative to the first ultrasonic horn upon ultrasonic vibration of the first ultrasonic horn at the predetermined frequency and to operate in an ultrasonic cavitation mode of the agitating members corresponding to the predetermined frequency.

11. The process as set forth in claim 10 wherein the second ultrasonic horn comprises a second plurality of discrete agitating members in contact with and extending transversely outward from the outer surface of the second ultrasonic horn intermediate the inlet port and the outlet port of the housing in longitudinally spaced relationship with each other, the agitating members and the second ultrasonic horn being constructed and arranged for dynamic motion of the agitating members relative to the second ultrasonic horn upon ultrasonic vibration of the second ultrasonic horn at the predetermined frequency and to operate in an ultrasonic cavitation mode of the agitating members corresponding to the predetermined frequency and the aqueous effluent being treated in the chamber.

12. The process as set forth in claim 11 wherein at least one of the agitating members of the first ultrasonic horn comprises a T-shape and at least one of the agitating members of the second ultrasonic horn comprises a T-shape.

13. The process as set forth in claim 6 wherein the housing comprises a first longitudinal end and a second longitudinal end and, wherein the treatment chamber further comprises a mesh substrate located laterally between the first waveguide assembly and the second waveguide assembly and extends from the first longitudinal end of the housing to the second longitudinal end of the housing.

14. The process as set forth in claim 13 wherein the mesh substrate comprises a material selected from the group consisting of stainless steel, polyethylene, polypropylene, and perfluorinated materials.

15. A process of delivering functional compounds to a substrate, the process comprising:

introducing an aqueous effluent comprising at least one functional compound through at least one inlet port of an elongate housing of a treatment chamber, the housing comprising longitudinal opposite ends and an interior space, the housing further being generally closed at at least one longitudinal end, and wherein the housing comprises an adsorbent located within the interior space;

ultrasonically energizing and electrically charging the adsorbent at a predetermined ultrasonic frequency and electrode potential within the housing using a first electrically-charged elongate ultrasonic waveguide assembly and a second electrically-charged elongate ultrasonic waveguide assembly, wherein both the first waveguide assembly and the second waveguide assembly independently comprise terminal ends, wherein the terminal end of the first waveguide assembly faces towards the terminal end of the second waveguide assembly, the first waveguide assembly further comprising a first elongate ultrasonic horn and the second waveguide assembly further comprising a second elongate ultrasonic horn;

adsorbing the functional compound to the surface of the energized and electrically charged adsorbent to form a carrier component of a delivery system;

exhausting the carrier component from at least one outlet port of the housing; and contacting the carrier component with a substrate.

16. The process as set forth in claim 15 wherein the first ultrasonic horn and the second ultrasonic horn are independently disposed at least in part intermediate the inlet port and the outlet port of the housing and each independently have an outer surface, wherein the adsorbent is located on the outer surface of at least one of the first ultrasonic horn and second ultrasonic horn for contact with the aqueous effluent flowing within the housing from the inlet port to the outlet port.

17. The process as set forth in claim 16 wherein the electrode potential is produced by electrically contacting both the first ultrasonic horn and the second ultrasonic horn with an electrical current source.

18. The process as set forth in claim 16 wherein the second ultrasonic horn further is configured in a hollow-cylinder shape, wherein the first ultrasonic horn is disposed lengthwise within the cylinder of the second ultrasonic horn.

19. The process as set forth in claim 16 wherein the second ultrasonic horn further is U-shaped and thereby comprises a first arm member and a second arm member, and wherein the first ultrasonic horn is disposed between the first arm member and second arm member of the second ultrasonic horn.

20. A process of delivering functional compounds to a substrate, the process comprising:

introducing an aqueous effluent comprising at least one functional compound through at least one inlet port of an elongate housing of a treatment chamber, the housing comprising longitudinal opposite ends and an interior space, the housing further being generally closed at at least one longitudinal end, and wherein the housing comprises an adsorbent located within the interior space;

ultrasonically energizing and electrically charging the adsorbent at a predetermined ultrasonic frequency and electrode potential within the housing using a first electrically-charged elongate ultrasonic waveguide assembly and a second electrically-charged elongate ultrasonic waveguide assembly, wherein both the first waveguide assembly and the second waveguide assembly independently comprise terminal ends, wherein the terminal end of the first waveguide assembly faces away from the terminal end of the second waveguide assembly, the first waveguide assembly further comprising a first elongate ultrasonic horn and the second waveguide assembly further comprising a second elongate ultrasonic horn;

adsorbing the functional compound to the surface of the energized and electrically charged adsorbent to form a carrier component of a delivery system;

exhausting the carrier component from at least one outlet port of the housing; and contacting the carrier component with a substrate.

* * * * *